US008543420B2

(12) United States Patent
Darby et al.

(10) Patent No.: US 8,543,420 B2
(45) Date of Patent: Sep. 24, 2013

(54) PATIENT-SPECIFIC CONTENT DELIVERY METHODS AND SYSTEMS

(75) Inventors: Kristin Darby, Boston, MA (US); Ravi Kalathil, Waltham, MA (US); Kurt Littlefield, Derry, NH (US); Maria Burke, Waxhaw, NC (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 684 days.

(21) Appl. No.: 12/233,126

(22) Filed: Sep. 18, 2008

(65) Prior Publication Data
US 2009/0076856 A1    Mar. 19, 2009

Related U.S. Application Data

(60) Provisional application No. 60/973,676, filed on Sep. 19, 2007.

(51) Int. Cl.
G06F 19/00    (2011.01)

(52) U.S. Cl.
USPC ............................................................ 705/3

(58) Field of Classification Search
USPC .................. 705/2–4; 600/300–301; 280/1; 345/327; 434/262; 707/101
See application file for complete search history.

(56) References Cited

U.S. PATENT DOCUMENTS

| | | |
|---|---|---|
| 3,637,997 A | 1/1972 | Petersen |
| 4,245,244 A | 1/1981 | Lijewski et al. |
| 5,025,523 A | 6/1991 | Zappa et al. |
| 5,276,611 A | 1/1994 | Ghiraldi |
| 5,283,560 A | 2/1994 | Bartlett |
| 5,293,470 A | 3/1994 | Birch et al. |
| 5,304,173 A | 4/1994 | Kittrell et al. |
| 5,345,250 A | 9/1994 | Inoue et al. |
| 5,367,316 A | 11/1994 | Ikezaki |

(Continued)

FOREIGN PATENT DOCUMENTS

| | | |
|---|---|---|
| DE | 10049393 A1 | 4/2002 |
| EP | 1271386 A2 | 1/2003 |

(Continued)

OTHER PUBLICATIONS

"Interactive Hospital Menus Go Prime Time" Internet Article, Dietary Manager Magazine, (Online) Apr. 2007, pp. 29-31, XP002505453, Retrieved from the internet: http://www.dmaonline.org/Publications/articles/2007_04 Interactive.pdf.

(Continued)

Primary Examiner — John Pauls
(74) Attorney, Agent, or Firm — Nutter McClennen & Fish LLP; David J. Powsner

(57) ABSTRACT

Methods and systems for delivery of digital data in connection with medical treatment and patient care include detecting a current medical condition of a patient receiving medical treatment and delivering electronic informational data to the patient over a network. The informational data can be selected for delivery based on the current medical condition of the patient. The informational data can includes a plurality of informational data content options, and the patient can choose one or more of the informational data content options for delivery to the patient over the network. The chosen content can be displayed to the patient on a digital data display device, such as a touch screen monitor.

28 Claims, 14 Drawing Sheets

(56) References Cited

U.S. PATENT DOCUMENTS

| | | |
|---|---|---|
| 5,389,947 A | 2/1995 | Wood et al. |
| 5,396,281 A | 3/1995 | Maeda |
| 5,401,238 A | 3/1995 | Pirazzoli |
| 5,434,626 A | 7/1995 | Hayashi et al. |
| 5,690,813 A | 11/1997 | Coale |
| 5,781,442 A | 7/1998 | Engleson et al. |
| 5,798,752 A | 8/1998 | Buxton et al. |
| 5,838,291 A | 11/1998 | Ohshima et al. |
| 5,850,221 A | 12/1998 | Macrae et al. |
| 5,858,239 A | 1/1999 | Kenley et al. |
| 5,865,745 A | 2/1999 | Schmitt et al. |
| 5,900,859 A | 5/1999 | Takishita et al. |
| 5,903,211 A | 5/1999 | Flego et al. |
| 5,933,136 A * | 8/1999 | Brown .................. 715/741 |
| 5,946,659 A | 8/1999 | Lancelot et al. |
| 6,057,826 A | 5/2000 | Gaultier et al. |
| 6,067,157 A | 5/2000 | Altendorf |
| 6,118,430 A | 9/2000 | Igari |
| 6,143,181 A | 11/2000 | Falkvall et al. |
| 6,146,523 A | 11/2000 | Kenley et al. |
| 6,151,581 A | 11/2000 | Kraftson et al. |
| 6,228,047 B1 | 5/2001 | Dadson et al. |
| 6,335,725 B1 | 1/2002 | Koh et al. |
| 6,335,761 B1 | 1/2002 | Glen et al. |
| 6,359,631 B2 | 3/2002 | DeLeeuw |
| 6,462,786 B1 | 10/2002 | Glen et al. |
| 6,469,695 B1 | 10/2002 | White |
| 6,493,002 B1 | 12/2002 | Christensen |
| 6,493,747 B2 | 12/2002 | Simmon et al. |
| 6,507,868 B2 | 1/2003 | Simmon et al. |
| 6,574,503 B2 | 6/2003 | Ferek-Petric |
| 6,684,379 B2 | 1/2004 | Skoll et al. |
| 6,736,789 B1 | 5/2004 | Spickermann |
| 6,738,052 B1 | 5/2004 | Manke et al. |
| 6,746,398 B2 | 6/2004 | Hervy et al. |
| 6,820,050 B2 | 11/2004 | Simmon et al. |
| 6,912,664 B2 | 6/2005 | Ranganathan et al. |
| 6,919,269 B2 | 7/2005 | Schneegans et al. |
| 6,982,727 B2 | 1/2006 | Baer et al. |
| 7,015,899 B2 | 3/2006 | Kim |
| 7,038,588 B2 | 5/2006 | Boone et al. |
| 7,044,927 B2 | 5/2006 | Mueller et al. |
| 7,088,343 B2 | 8/2006 | Smith et al. |
| 7,134,966 B1 | 11/2006 | Tice |
| 7,154,397 B2 | 12/2006 | Zerhusen et al. |
| 7,170,500 B2 | 1/2007 | Canova, Jr. |
| 7,185,282 B1 * | 2/2007 | Naidoo et al. ............. 715/718 |
| 7,188,151 B2 | 3/2007 | Kumar et al. |
| 7,190,352 B2 | 3/2007 | Ling et al. |
| 7,215,991 B2 | 5/2007 | Besson et al. |
| 7,284,262 B1 | 10/2007 | Meric et al. |
| 7,336,187 B2 | 2/2008 | Hubbard, Jr. et al. |
| 7,351,340 B2 | 4/2008 | Connell et al. |
| 7,584,108 B2 | 9/2009 | Brown |
| 7,627,334 B2 | 12/2009 | Cohen et al. |
| 7,685,005 B2 * | 3/2010 | Riff et al. ................ 705/3 |
| 7,801,746 B2 | 9/2010 | Moll et al. |
| 8,182,440 B2 | 5/2012 | Cruz et al. |
| 2001/0005115 A1 | 6/2001 | Busio et al. |
| 2001/0011036 A1 | 8/2001 | Miyamoto et al. |
| 2001/0016056 A1 | 8/2001 | Westphal et al. |
| 2001/0034614 A1 | 10/2001 | Fletcher-Haynes et al. |
| 2001/0045395 A1 | 11/2001 | Kitaevich et al. |
| 2001/0056226 A1 | 12/2001 | Zodnik et al. |
| 2002/0032385 A1 | 3/2002 | Raymond et al. |
| 2002/0035637 A1 | 3/2002 | Simmon et al. |
| 2002/0082728 A1 | 6/2002 | Mueller et al. |
| 2002/0107449 A1 | 8/2002 | Roeher |
| 2002/0163178 A1 | 11/2002 | Williams |
| 2002/0198473 A1 | 12/2002 | Kumar et al. |
| 2003/0001743 A1 | 1/2003 | Menard |
| 2003/0018395 A1 | 1/2003 | Crnkovich et al. |
| 2003/0069481 A1 | 4/2003 | Hervy et al. |
| 2003/0083901 A1 | 5/2003 | Bosch et al. |
| 2003/0141981 A1 | 7/2003 | Bui et al. |
| 2003/0197690 A1 | 10/2003 | Zimenkov |
| 2003/0220607 A1 | 11/2003 | Busby et al. |
| 2004/0021673 A1 | 2/2004 | Alessi et al. |
| 2004/0111293 A1 | 6/2004 | Firanek et al. |
| 2004/0111294 A1 | 6/2004 | McNally et al. |
| 2004/0176984 A1 | 9/2004 | White et al. |
| 2004/0193448 A1 | 9/2004 | Woodbridge et al. |
| 2004/0220832 A1 | 11/2004 | Moll et al. |
| 2004/0260478 A1 | 12/2004 | Schwamm |
| 2004/0261037 A1 | 12/2004 | Ording et al. |
| 2005/0021369 A1 | 1/2005 | Cohen et al. |
| 2005/0062238 A1 * | 3/2005 | Broadfield et al. ............ 280/1 |
| 2005/0081164 A1 | 4/2005 | Hama et al. |
| 2005/0139515 A1 | 6/2005 | Gu et al. |
| 2005/0213425 A1 | 9/2005 | Wang et al. |
| 2006/0058603 A1 | 3/2006 | Dave et al. |
| 2006/0066581 A1 | 3/2006 | Lyon et al. |
| 2006/0176403 A1 | 8/2006 | Gritton et al. |
| 2006/0190297 A1 | 8/2006 | Glass et al. |
| 2006/0231108 A1 | 10/2006 | Novatzky et al. |
| 2007/0020341 A1 | 1/2007 | Miyata |
| 2007/0040787 A1 | 2/2007 | Saha |
| 2007/0046596 A1 | 3/2007 | Sakakibara et al. |
| 2007/0078878 A1 * | 4/2007 | Knable ................ 707/101 |
| 2007/0112603 A1 | 5/2007 | Kauthen et al. |
| 2007/0125709 A1 | 6/2007 | Nigam |
| 2007/0130287 A1 * | 6/2007 | Kumar et al. ............ 709/217 |
| 2007/0168229 A1 * | 7/2007 | Kim ..................... 705/2 |
| 2007/0223877 A1 | 9/2007 | Kuno |
| 2008/0015487 A1 | 1/2008 | Szamosfalvi et al. |
| 2008/0097283 A1 * | 4/2008 | Plahey ................. 604/29 |
| 2008/0097550 A1 * | 4/2008 | Dicks et al. ............ 607/59 |
| 2008/0154177 A1 | 6/2008 | Moubayed et al. |
| 2008/0268413 A1 * | 10/2008 | Leichner ................ 434/262 |
| 2008/0275721 A1 * | 11/2008 | Nagai et al. ............ 705/2 |
| 2009/0008331 A1 | 1/2009 | Wilt et al. |
| 2009/0037216 A1 | 2/2009 | Bluemler et al. |
| 2009/0076338 A1 | 3/2009 | Zdeblick et al. |
| 2009/0076856 A1 | 3/2009 | Darby et al. |
| 2010/0137693 A1 | 6/2010 | Porras et al. |
| 2011/0105979 A1 | 5/2011 | Schlaeper et al. |

FOREIGN PATENT DOCUMENTS

| | | |
|---|---|---|
| EP | 2043014 A1 | 4/2009 |
| JP | 2003006331 A | 1/2003 |
| JP | 2008284229 A | 11/2008 |
| KR | 2001-091801 A | 10/2001 |
| KR | 2002-170210 * | 10/2003 |
| WO | WO-9628086 | 9/1996 |
| WO | WO-0207591 | 1/2002 |
| WO | WO-2004070995 A2 | 8/2004 |
| WO | WO-2006020862 A2 | 2/2006 |
| WO | WO-2006122325 | 11/2006 |
| WO | WO-2007033600 A1 | 3/2007 |
| WO | WO-2007035696 | 3/2007 |
| WO | WO-2007/040963 | 4/2007 |
| WO | WO-2007/040975 | 4/2007 |
| WO | WO-2007/044877 | 4/2007 |
| WO | WO-2007/038147 | 4/2007 |
| WO | WO-2007/053683 | 5/2007 |
| WO | WO-2007049163 A2 | 5/2007 |
| WO | WO-2007049253 A2 | 5/2007 |
| WO | WO-2007120904 A2 | 10/2007 |
| WO | WO-2007126360 A1 | 11/2007 |
| WO | WO-2008008281 A2 | 1/2008 |
| WO | WO-2009002620 A1 | 12/2008 |

OTHER PUBLICATIONS

"PatientLife:)System TM . . . your comprejensive solution for patient-sentered care," Internet Article, Brouchure, Getwellnetwork, Inc., (Online) Mar. 18, 2006, pp. 1-6, XP002505452, http://web.archive.org/web/20060318175409/http://www.getwellnetwork.com/pdfs/GWNProductBrochure.pdf.

European Search Report, EP Application No. 08164693.7, Mailed Dec. 10, 2008.

Intel 510k Summary, Jun. 27, 2008.

Nakamoto, Telemedicine System for Patients on Continuous Ambulatory Peritoneal Dialysis, Peritoneal Dialysis International, vol. 27, 2007.

NHS Lothian Implements Intels Personal Health System to Manage Patients with Chronic Conditions, Intel, Feb. 24, 2009.

International Search Report issued Jul. 23, 2007, for Application No. PCT/US2006/42650 (11 Pages).

[No Author] Dialysis data acquisition and management system: Finesse® Professional. Fresenius Medical Care. Product information sheet. 2002, 2 pages.

[No Author] Dialysis data management system FinProDB: Finesse® Professional Database. Fresenius Medical Care. Product information sheet. 2004, 2 pages.

[No Author] Exalis: Dialysis data management tool. Gambro Lundia AB. Product information sheet. Jun. 2002, 8 pages.

[No Author] Finesse®. Fresenius Medical Care. Retrieved Jun. 17, 2009 from http://fmc.intra.fresenius.de. 2008, 2 pages.

[No Author] Finesse® HomeHemo Dialysis (TI 1025 e, v2.01). Medvision AG. Product information sheet. 2004, 6 pages.

[No Author] Therapy Data Management System: Data acquisition, data management and quality assurance as an integrated solution. Fresenius Medical Care. Product information sheet. 2007, 12 pages.

* cited by examiner

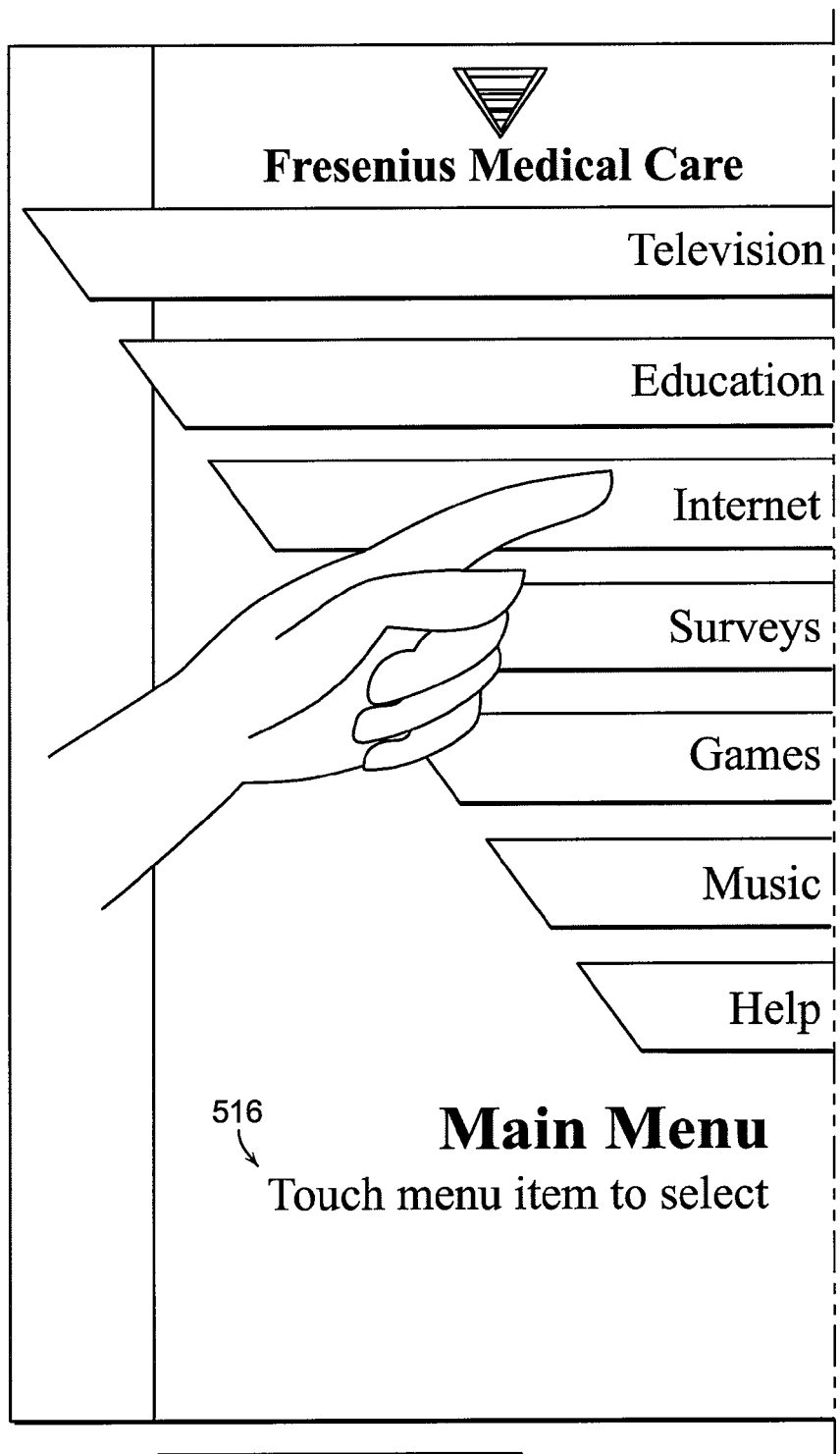
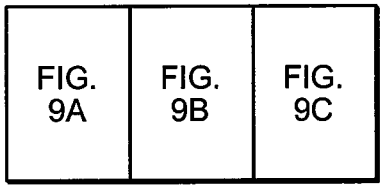
FIG. 9A
FIG. 9

PATIENT-SPECIFIC CONTENT DELIVERY METHODS AND SYSTEMS

This application claims the benefit of filing of U.S. patent application Ser. No. 60/973,676, filed Sep. 19, 2007, the teachings of which are incorporated herein by reference.

BACKGROUND OF THE INVENTION

Dialysis is an important treatment regimen for a variety of chronic diseases. To meet the need for regular care, patients typically travel to hospitals or dialysis centers that are designed for efficient and routine dialysis therapy. Typically, a nurse or patient care technician oversees the treatment sessions, assists the patients, and records patient information, such as patient vitals, treatment details, and billing information.

Like other health care facilities, one difficulty that dialysis treatment centers may encounter is maintaining patient participation in treatment and, thereby, improving medical outcome. To large extent this is accomplished by providing educational materials to patients. The hope and theory are that well informed patients will pay special attention to their own treatment, not miss appointments, and keep their health care providers apprised of any changes in condition or circumstance not otherwise revealed by routine medical testing. Unfortunately, this entails distributing a large amount of information to patients. However, material regarding each patient's treatment may not always be readily identifiable or accessible when the patient needs or desires it. Furthermore, even where the health care provider is able to provide materials of potential interest, patients still may not feel they are actively involved with the treatment process, and therefore be less motivated to follow suggested treatment.

An object of the invention is to provide improved methods and systems for health care provision.

A related object is to provide such methods and systems as can be used to improve delivery of information in connection with health care provision.

A further object is to provide such methods and systems as can be used to increase patient participation and satisfaction with health care provision.

A still further object is to provide such methods and systems as can be used in connection with dialysis treatment and/or otherwise in the provision of health care.

SUMMARY OF THE INVENTION

The foregoing objects are among those attained by the invention which provides, in some aspects, a method of driving an electronic data interface (e.g., a computer display or a "touch screen") in connection with medical treatment of a patient. Such a method includes detecting a current medical condition of the patient and driving an electronic data interface in order to (i) deliver content to the patient based on that medical condition, (ii) query the patient based on that medical condition, and/or (iii) stimulate participation of the patient in his or her care based on that medical condition. Interactions with the patient are tailored to improve the clinical outcome of the patient's treatment based on the medical condition through education and/or patient participation.

Related aspects of the invention provide such methods as used in connection with the delivery of hemodialysis and/or peritoneal dialysis treatment of a patient.

Related aspects of the invention provide such methods in which the step of driving the electronic data interface includes providing textual, audio, video and/or other education material to the patient. According to further related aspects of the invention, the step of driving the electronic data interface includes providing questions to and collecting responses from the patient, e.g., as part of a survey, questionnaire, or other interrogatory process. According to further related aspects of the invention, the step of driving the electronic data interface includes hosting a game (e.g., a "video" board or card game) in which the patient participates, e.g., on the touch screen.

According to further aspects of the invention, the step of detecting the current medical condition of a patient includes receiving clinical data regarding the patient's current medical condition from medical apparatus, e.g., a hemodialysis or peritoneal dialysis machine, coupled to the patient. Related aspects of the invention include transmitting clinical data regarding the patient's current medical condition from such medical apparatus to a clinical database system and, further, driving the electronic data interface in accord with information pertaining to such condition received from that system.

Still further aspects of the invention provide methods as described above in which the current medical condition includes a clinical condition of the patient, including, at least one of blood pressure, heart rate, and blood potassium level. According to aspects of the invention practiced in connection with the provision of hemodialysis or peritoneal dialysis, that condition can include other clinical measurements sensed by equipment providing such treatment to the patient.

Further aspects of the invention provide methods as described above in which the step of driving the electronic data interface includes (i) delivering content to the patient based the patient's medical history and/or medical record, (ii) querying the patient based on his/her medical history and/or medical record, and/or (iii) stimulating participation of the patient in his or her care based such medical history and/or medical record.

Still yet further aspects of the invention provide methods as described above that include storing medical records and/or other patient-specific information in a clinical database system.

Yet still further aspects of the invention provide methods as described above in which the step of driving the electronic data interface includes displaying to the patient a plurality of mode and/or content selection options, permitting the patient to select from among those options, and further driving the electronic data interface in accord with the patient selection. According to related aspects of the invention, such a methodology can be used to permit the patient to select among modes for the provision of textual, audio, video and/or other educational material, and, optionally, within that mode, to select specific content to be delivered; the provision of a survey or questionnaire, and, optionally, within that mode, to select a specific survey or questionnaire to answer; and/or the playing of a game or other patient-participatory experience and, optionally, within that mode, to select a specific game to play.

According to further related aspects of the invention, the steps displaying to the patient mode selection options, permitting the patient to select from among those options, and/or further driving the electronic data interface in accord with the patient selection can include restricting and/or expanding such selections based on the patient's medical condition and/or his her compliance with medical treatment requirements, goals, or milestones. Thus, by way of non-limiting example, a patient who has satisfactorily brought down his blood pressure may be entitled to a broader range of mode and/or content options, while a patient who has not satisfactorily brought down his blood pressure may be limited to a restricted range of options.

Further aspects of the invention provide methods as described above in which the step of driving the electronic data interface includes selecting among one or more of the afore-mentioned modes and/or educational content to be delivered in connection therewith in accord with a pre-programmed algorithm.

Still further related aspects of the invention provide such methods as enable a medical care professional to select among one or more of the aforementioned modes and/or to select educational content to be delivered to the patient in connection therewith.

Yet still further aspects of the invention provide methods as described above including driving the electronic data interface to authenticate the patient before one or more of (i) delivering content thereto based on a medical condition, (ii) querying the patient based on that medical condition, and/or (iii) stimulating participation of the patient in his or her care based on that medical condition.

In another embodiment, a method of delivering patient-specific content includes providing a digital data display device configured to display data to a patient receiving medical treatment and authenticating the patient as a valid user of the digital data display device. The method can further include transmitting first data to the digital data display device from at least one database, wherein the first data is chosen for transmission based on at least real-time data related to medical treatment of the authenticated patient. The authenticated patient can be allowed to choose from the first data additional data for transmission from the at least one database to the digital data display device.

Further aspects of the invention provide medical treatment apparatus and systems operating in accord with the methodologies discussed above. In one such aspect, by way of non-limiting example, the invention provides a patient-specific content delivery system that includes a computer-driven interface device (e.g., a display and/or touch screen) configured to display and/or receive information to/from a patient for purposes of any of (i) delivering content to the patient based on that medical condition, (ii) querying the patient based on that medical condition, and/or (iii) stimulating participation of the patient in his or her care based on that medical condition. Such an interface device can, according to aspects of the invention be configured as part of, or to operate connection with, hemodialysis equipment, peritoneal dialysis equipment, or other patient care equipment.

According to further aspects of the invention, medical treatment apparatus and systems as described above can include a clinical database system in electronic communication that stores information pertaining to real-time medical conditions of a patient undergoing medical treatment. Such a clinical database system can, according to related aspects of the invention, store medical records and other patient-specific information (e.g., medical histories) for use in displaying and/or receiving information to/from the interface device.

These and other aspects of the invention relating to patient care are evident in the drawings and in the detailed description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Described herein are methods and devices for medical treatment and patient care, particularly, by way of non-limiting example, in the context of dialysis centers—though applicable in a range of health care settings. Those methods and devices, which provide for improved clinical outcome of patient care through education and/or patient participation, include driving a digital data interface (e.g., a computer display or touch screen) accessible by the patient in accord with that patient's current medical condition. More specifically, that interface can be driven to (i) deliver content to the patient based on a medical condition of the patient, (ii) query the patient based on that medical condition, and/or (iii) stimulate participation of the patient in his or her care based on that medical condition (collectively, "condition-based information transfer"), all in accord with the patient's blood pressure, potassium levels, or other medical conditions.

Figure 1:
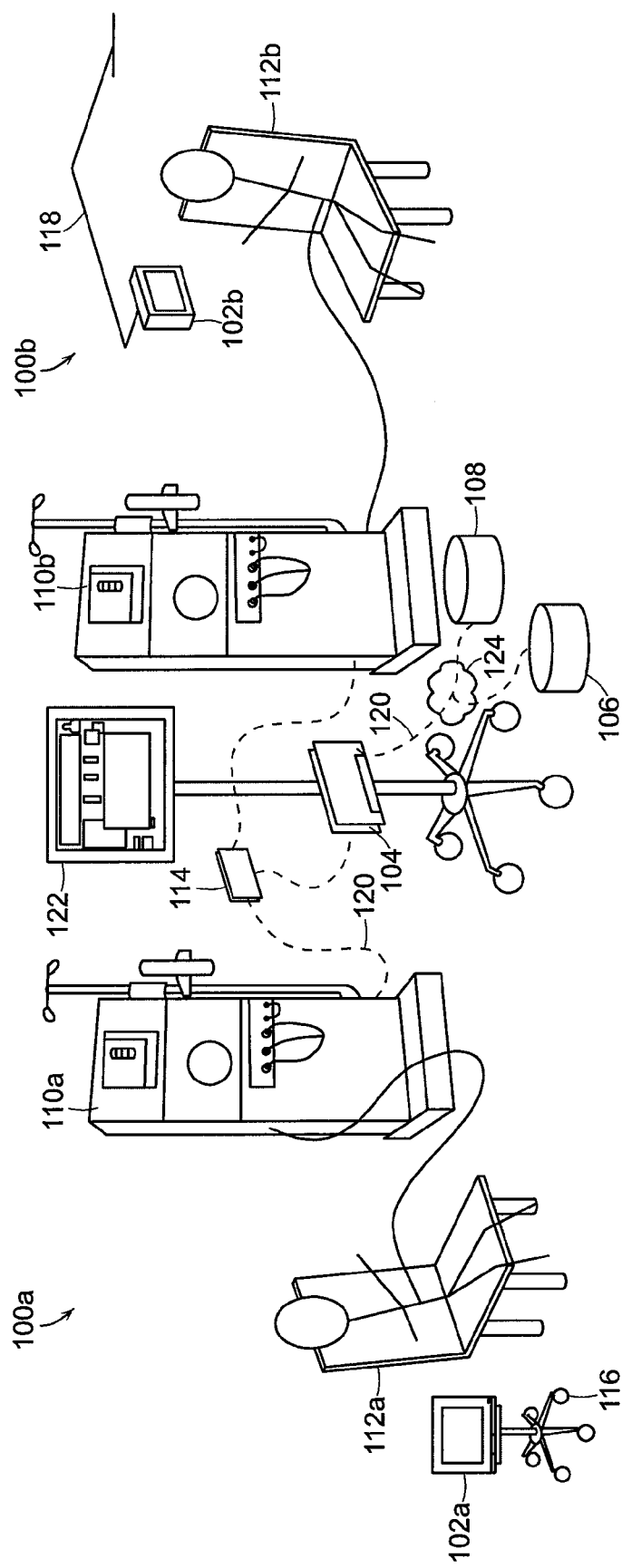
FIG. 1 depicts a plurality of digital data display devices according to the invention, as well as a plurality of medical treatment apparatus (e.g., dialysis machines) with which such devices may be used.

FIG. 1 illustrates patient treatment stations 100a, 100b according to one practice of the invention. The patient treatment stations 100a, 100b comprise an electronic data interface (e.g., a display screen, a computer-driver interface, or a touch screen) 102a, 102b that provides a visual and possibly tactile interface with a user and a digital processor 104 that controls the display screen 102a, 102b (e.g., vis-à-vis the display of prompts, as well as the input, display, communication, collection and/or storage of the information therefrom and thereto), and that interfaces with other such database systems 106, 108 (data storage mechanisms such as databases, servers, or otherwise), as well as with medical treatment apparatus, such as dialysis machines 110a, 110b (hemodialysis or peritoneal dialysis treatment). The patient treatment station 100a, 100b does not necessarily require a physical keyboard for user input, thereby greatly reducing the risk of patient infection. In addition, the display screen 102a, 102b interface and the method of condition-based information transfer can allow customized content to be automatically and/or manually chosen by a patient 112a, 112b for delivery to the patient 112a, 112b in real time based on a medical condition of the patient 112a, 112b at the machines 110a, 110b.

The condition-based information transfer includes one or both of receiving medical condition information from the patient treatment station 100a, 100b and delivering content from the databases 106, 108 to the patients 112a, 112b (via the screens 102a, 102b) based on the received medical condition information. The customized information delivered to the display screens 102a, 102b can include textual, audio, video, and/or other education material that includes clinical data, which can facilitate the improvement of clinical outcome through education and patient participation in their own care, and entertainment, which can improve overall patient satisfaction with their treatment, improve patient compliance with prescribed treatment times, and provide a relaxing atmosphere that can positively affect overall clinical outcomes. The customized information received from the patients 112a, 112b can include medical data automatically gathered from the machines 110a, 110b and/or from other devices coupled to the patients 112a, 112b. The patients 112a, 112b can also transfer information to the processor 104 in response to content on the display screens 102a, 102b, such as choices of additional content for delivery or answers to survey questions.

As shown, the stations 100a, 100b are each associated with a medical treatment apparatus 110a, 110b (in this embodiment, hemodialysis machines) of the type commonly known in the art. The display screens 102a, 102b of the stations 100a, 100b are in electronic communication with the processor 104 (or otherwise coupled thereto) for use by a user such as a patient 112a, 112b being treated with the dialysis machines 110a, 110b, a nurse, a patient care technician, or other health care provider. Although two stations 100a, 100b are shown, those skilled in the art will appreciate that the processor 104 and the storage mechanisms 106, 108 may support more than or less than two stations. Furthermore, the stations 100a, 100b can be in locations remote from each other and/or the processor 104. For example, the stations 100a, 100b can be located in a clinical setting (e.g., a hospital or a hemodialysis clinic) or a non-clinical setting (e.g., at a home of a dialysis patient receiving peritoneal dialysis using a home-based system).

The stations 100a, 100b can each include a touch screen display 102a, 102b, the digital data processor 104, and an adapter 114. The touch screen displays 102a, 102b can each include a conventional device of that type known in the art for visual and/or tactile interface with an operator—here, patient 112a, 112b—operated in accord with the teachings hereof. The units 102a, 102b can be based on liquid crystal display technology, cathode ray display technology, or otherwise. Though the illustrated embodiment relies on color display technology, other embodiments may utilize monochrome (e.g., employing shading, hashing, or other visual indicators in place of the colorations discussed below). The displays 102a, 102b are sized and provides resolution sufficient to display and collect information of the type described or are otherwise suitable for the digital data environment for which it is used. Preferably the displays 102a, 102b can be adapted for ready cleaning and/or sanitization, particularly when used in a clinical environment where multiple people typically use the displays 102a, 102b.

Additionally, while the displays 102a, 102b preferably include touch screens, the display devices 102a, 102b can include any device capable of displaying information to a user, e.g., a personal computer, a television, a portable digital device, or any other electronic display device. Furthermore, the displays 102a, 102b can have any configuration where they may be made easily, comfortably accessible to the patient 112a, 112b, such as on a rolling stand 116 (left display 102a), on an adjustable arm 118 (right display 102b), or otherwise. In other embodiments, the displays 102a, 102b may be more fully portable (e.g., lightweight and with carrying handles), fixed (e.g., wall-mounted or cabinet-mounted) or otherwise—all in the conventional manner of clinically-deployed medical data entry devices.

The displays 102a, 102b can be adapted to provide an ergonomic work station such that data entry puts a minimal stress on the patients 112a, 112b. The height and angle of the displays 102a, 102b can facilitate data entry and minimize the risk of repetitive stress disorders. The height and angle of the displays 102a, 102b also can make their screens less visible to a casual onlooker such as another patient or ambulance driver walking by, which helps protect the confidentiality of any patient data being displayed. The illustrated displays 102a, 102b can be set to display a neutral screen saver after a set or variable amount of time of system inactivity to further protect the confidentiality of such patient data.

The digital data processor 104 can include an embedded processor, personal computer; workstation, minicomputer, mainframe or other digital data processing device of the type known in the art, as adapted in accord with the teachings hereof. The digital data processor 104 may be a stand alone device or may be integral to one or more other components of the illustrated system, e.g., the touch screens 102a, 102b and/or medical treatment apparatus 110a, 110b. It may, moreover, be coupled for communication over communication links 120 with the touch screen displays 102a, 102b and the adapter 114 via any combination of wireless connection (e.g., BlueTooth, 802.1x, or otherwise), wired connection (Ethernet, backplane bus, or otherwise), or otherwise, all in the conventional manner known in the art.

Communication on one or more of the communication links 120 (which may include more or fewer linked connections than those shown in FIG. 1) may be secured with a mechanism such as IP security (IPsec), Transport Layer Security/Secure Socket Layer (TLS/SSL), wireless TLS (WTLS), secure Hypertext Transfer Protocol (S-HTTP), or any other security mechanism as would be appreciated by those skilled in the art.

The processor 104 can also be in communication with a data entry device such as a touch screen 122 that provides a visual and tactile interface with an administrator, e.g., a nurse, patient care technician, or other medical personnel. Through the touch screen 122, a user can coordinate input, display, communication, collection, and/or storage of data between the displays 102a, 102b, the processor 104, and/or the storage mechanisms 106, 108. Although only one touch screen 122 is shown in this embodiment, there may be any number of such data entry devices.

The database systems 106, 108 can each include a database, a data queue, a buffer, a local or remote memory device, random access memory (RAM), a cache, a server, or digital data storage device of the type known in the art, as adapted in accord with the teachings hereof. The databases 106, 108 are adapted to communicate with the displays 102a, 102b (via the processor 104) over one or more communication links 120 and possibly over a network 124, as described herein. Although the storage mechanisms 106, 108 are shown as separate elements from the processor 104 in this illustrated embodiment, the storage mechanisms 106, 108 can be integral to the processor 104, or the storage mechanisms 106, 108 can otherwise be combined into one storage mechanism or separated into one or more other storage mechanisms. Furthermore, the databases 106, 108 may communicate using the same or different network 124, which can itself include one ore more interconnected networks. One or both of the storage mechanisms 106, 108 may be secured using a variety of techniques, as those skilled in the art will appreciate.

In the illustrated embodiment, operation of the stations 100a, 100b in general, and of the touch screens 102a, 102b in particular, are controlled by the processor 104. To this end, and to the extent that this description attributes control and data processor functionality to the touch screens 102a, 102b, it will be appreciated that such control and data processing is provided indeed by the processor 104. Similarly, control and data processing of the storage mechanisms 106, 108 is provided indeed by the processor 104.

The adapter 114 provides communication coupling between the digital data processor 104 (and the storage mechanisms 106, 108) and the medical treatment apparatus (here, dialysis machines) 110a, 110b. In the illustrated embodiment, the adapter 114 is a Universal Serial Bus (USB) hub of the conventional type known in the art. In other embodiments, the adapter 114 can take on other form factors (electrical and/or physical), such as Ethernet, serial cabling, and so forth, suitable for transmitting data to/from the processor 104 and the apparatus 110a, 110b and/or the display 102a, 102b. Moreover, the illustrated adapter 114 can be supplanted by, or supplemented with, wireless communications (e.g., based on BlueTooth, 802.1x, and so forth), consistent with the aforesaid purpose. Regardless, the adapter 114 transmits data in a common protocol defined between the processor 104 and the treatment apparatus 110a, 110b. In the illustrated embodiment, the adapter 114 is a standalone device that is coupled with the processor 104 and the apparatus 110a, 110b via cabling, as shown, though in other embodiments it may be integral with one of more of the other system components (e.g., the processor 104, the storage mechanisms 106, 108, and/or the apparatus 110a, 110b).

In the illustrated embodiment, the displays 102a, 102b are used in connection with the medical treatment apparatus 110a, 110b to facilitate dialysis treatment of the patients 112a, 112b, as shown. Though the illustrated patients 112a, 112b are shown in chairs, those skilled in the art will appreciate that patients can receive treatment in prone or other positions, as well—all in the conventional manner known in the art.

Figure 2:
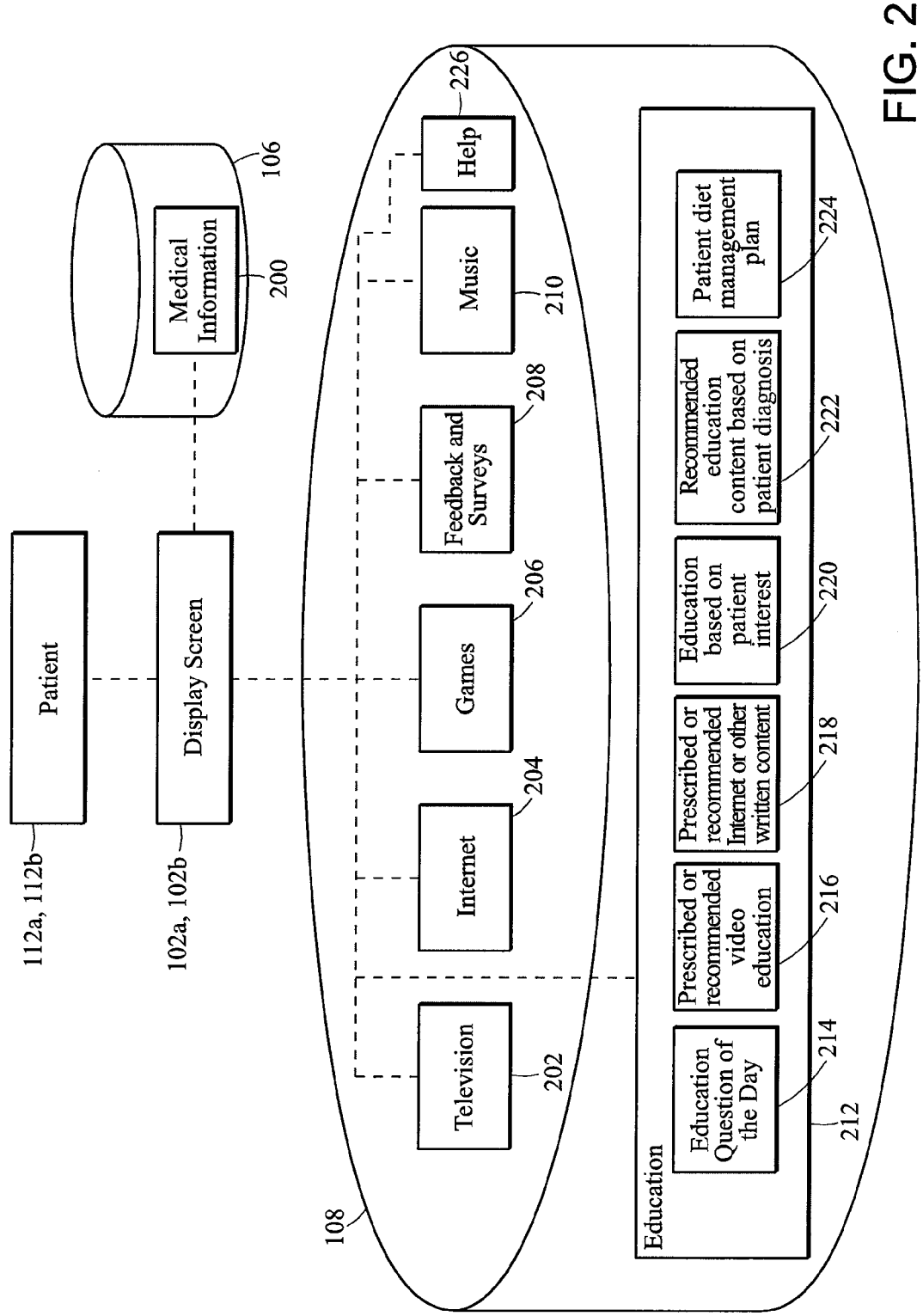
FIG. 2 depicts a schematic diagram of a database system according to the invention that stores data for display on a digital data display device.

Referring to FIG. 2, the storage mechanisms 106, 108 are shown in more detail. Information stored in one or both of the storage mechanisms 106, 108 can be delivered to the patients 112a, 112b via the display screens 102a, 102b (and the processor 104). The delivered information can be customized for each patient 112a, 112b, chosen in real time (e.g., on the fly) as the patient 112a, 112b is receiving, will soon receive, or has just received, medical treatment at the machines 110a, 110b. The delivered data can also be prescribed for the patients 112a, 112b by medical personnel before treatment and delivered after patient logon to the system.

As shown, each of the storage mechanisms 106, 108 can include information of different types. The information can be input into the storage mechanisms 106, 108 from a variety of sources. By way of non-limiting example, data can be manually input into the storage mechanisms 106, 108 by a user (e.g., at the touch screen 122), obtained from another database including the other one of the databases 106, 108, received from a monitoring device such as the machine 110a, and other similar data entry techniques.

One database 106 ("clinical database system 106" or "medical database 106") can store medical records and other patient-specific information 200 while the other database 108 (or "content database 108") can store content information for delivery to the display devices 102a, 102b. The medical information 200 in the medical database 106 can include programmed data and/or current treatment data. Programmed data generally includes data related to patient identification and previous patient care. Non-limiting examples of programmed data (generally, etiology data) include patient name, patient medical history, medical treatment history, lab results, treatment plans, dietician patient plans, ethnicity, demographics, and other types of similar data.

Current treatment data generally includes data gathered in real time while the patient 112a, 112b is being treated at the machines 110a, 110b, e.g., vital signs, dialysis results and performance, information on kidney function, survey results, phosphorus levels, video (e.g., surveillance using a web camera coupled to the touch screen 102a that can provide retinal tracking to monitor patient activity), etc. Current treatment data can be stored in the medical database 108 to create an archive of medication treatment information. The current treatment data (archived and/or from the instant treatment session) can be used by the processor 104 to determine what data from the content database 108 to deliver to a particular patient.

The content database 108 generally includes information that can be displayed on the display screens 102a, 102b, as further discussed below. The information can be dynamically chosen through analysis by the processor 104 such that the patients 112a, 112b can view information most relevant to their current medical status. Non-limiting examples of information that can be stored for delivery in the content database 108 include television data 202, network data 204 (in which case the content database 108 acts similar to a content server), games data 206, feedback and survey data 208, music data 210, education data 212, and other similar types of data. The education data 212 generally includes information that may be useful in educating the patients 112a, 112b about their medical condition and/or medical treatment. For example, the education data 212 can include an education question of the day 214, prescribed or recommended video education 216, prescribed or recommended Internet or other written content 218, education based on patient interest 220, recommended education content based on patient diagnosis 222, patient diet management plan data 224, and other types of similar data. The content database 108 can also include help information 226 related to use of the touch screens 102a, 102b, the machines 110a, 110b, and/or to data available to users through the touch screens 102a, 102b. Data can be categorized any way in the content database 108, including no categorization at all and categorization as more than one data type (e.g., as education data 212 and as games data 206).

Figure 3:
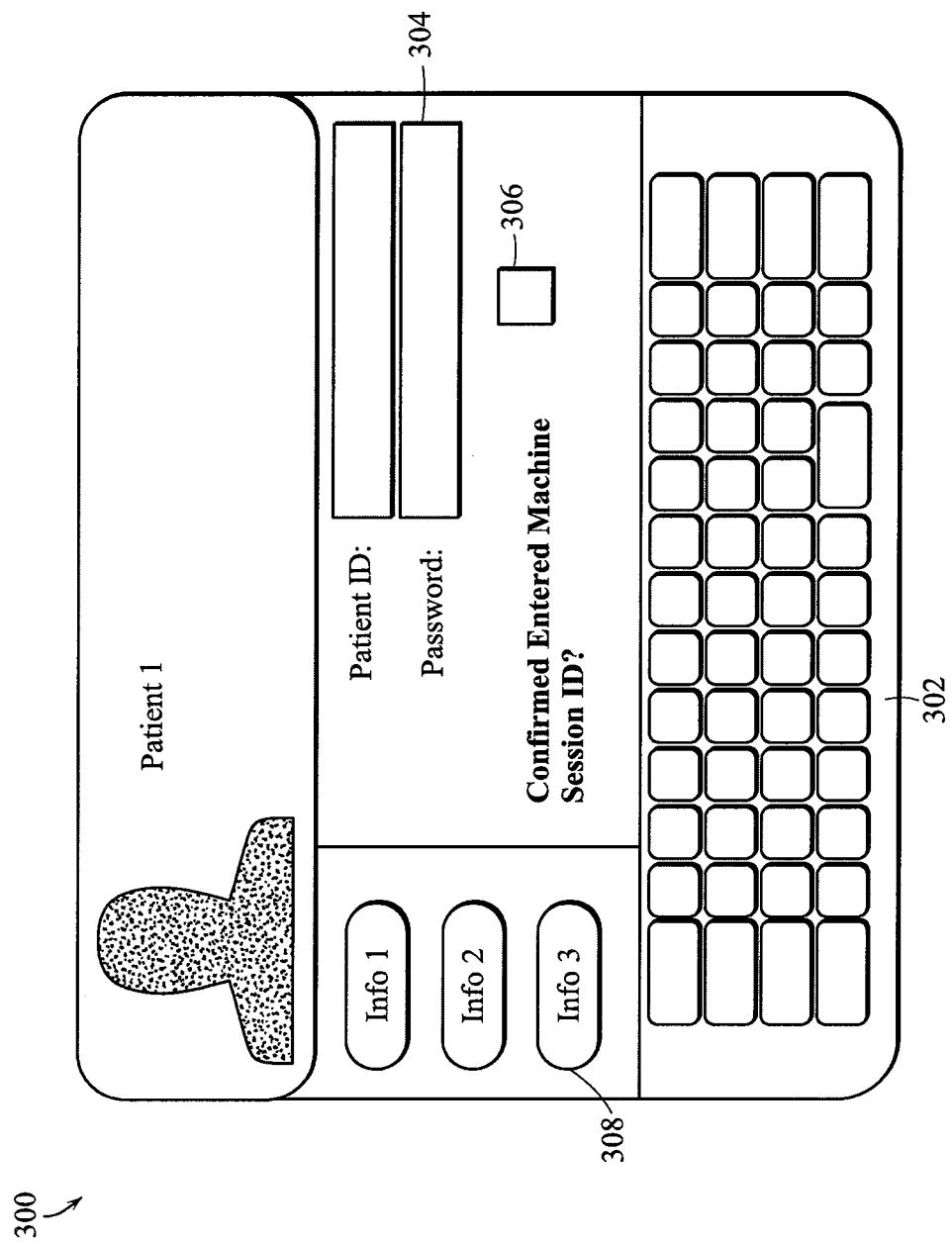
FIG. 3 depicts an authentication screen display of a digital data display device according to the invention that facilitates authentication of a patient that may use the digital data display device.

Referring to FIG. 3, in the illustrated embodiment, the touch screens 102a, 102b operate under control of the processor 104 to provide an entry screen 300 on the touch screens 102a, 102b, which the patients 112a, 112b (and/or medical personnel such as nurses and patient care technicians) can use to input letters, numbers, and/or other symbols via a keyboard icon 302 to be authenticated as a valid user and thereby access content from the processor 104 and/or the databases 106, 108 through the touch screens 102a, 102b. The entry screen 300 may or may not occupy a substantial entirety of the display screen 1002a, 102b (e.g., to the exclusion of other screens), as with all screens described herein.

Although authentication is illustrated in this example as occurring by the patients 112a, 112b at the touch screen 102a, 102b, the patients 112a, 112b may be authenticated in a similar way elsewhere (e.g., through another device in electronic communication with the touch screens 102a, 102b and/or the processor 104) and by a user other than the patients 112a, 112b (e.g., an administrator at the display screens 102a, 102b or the touch screen 122). Additionally, those skilled in the art will appreciate that authentication may occur in a multitude of other ways, e.g., using identification techniques such as voice imprint, fingerprint, retinal scan, biometric identification, though an access card, etc.

As shown in FIG. 3, the touch screens 102a, 102b can additionally, or alternatively, display text boxes 304, check boxes 306, button icons 308, or other widgets that a user can use to make input designations on the entry screen 300. Together, the icons 302, 304, 306, 308 (and/or any others displayed on the screen 102a, 102b) can be used to select and/or enter patient (user) identification. Furthermore, the icons 302, 304,306, 308 (and/or any others displayed on the screen 102a, 102b) can be organized in any configuration on the screens 102a, 102b, including different configurations on different ones of the screens 102a, 102b in communication with the processor 104. After authentication as a valid user, a user may be able to enter additional information through the entry screen 300, such as treatment information (e.g., blood pressure, pulse, treatment parameters) and post-treatment information (e.g., next scheduled patient visit, drug prescriptions, and so forth).

Figure 4:
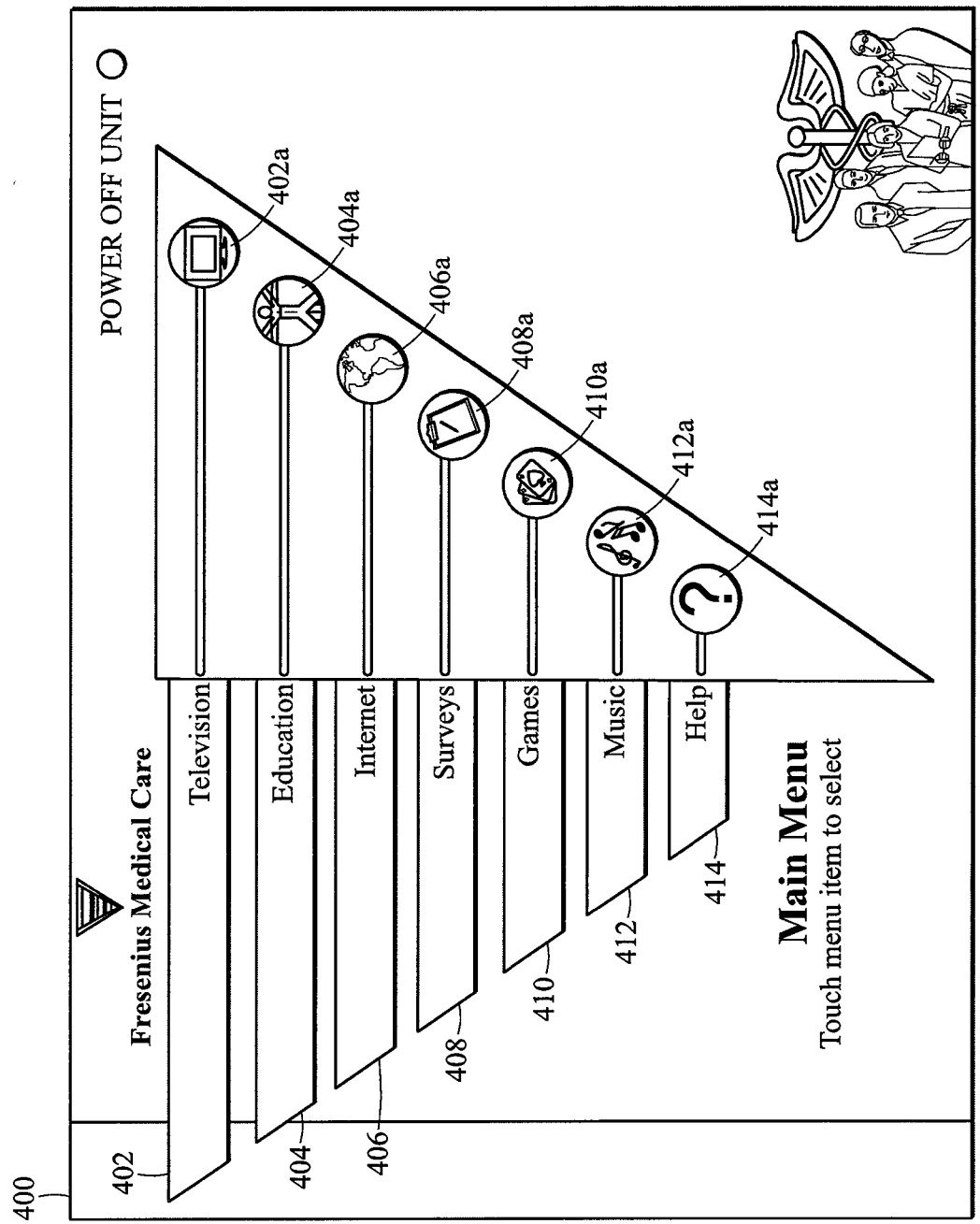
FIG. 4 depicts a menu screen display of a digital data display device according to the invention that facilitates selection of data for display.

FIG. 4 illustrates a menu screen 400 driven by the processor 104 to the touch screens 102a, 102b, e.g., at the start of a treatment session following user authentication (or before, as user authentication may occur after an initial selection on the menu screen 400, to facilitate selection of content for display on the touch screens 102a, 102b). The menu screen 400 displays a plurality of mode selection options 402, 404, 406, 408, 410, 412, 414 (e.g., content corresponding to data types in the medical database 106 and/or the content database 108) with a corresponding graphic 402a, 404a, 406a, 408a, 410a, 412a, 414a disposed adjacent to its corresponding text option 402, 404, 406, 408, 410, 412, 414 in the list. By way of non-limiting example, in the illustrated embodiment, the operator selects a content option by touching the options graphic 402a, 404a, 406a, 408a, 410a, 412a, 414a. However, those skilled in the art will appreciate that the method for selecting content from the list may vary (e.g., the user may touch the options text bar 402, 404, 406, 408, 410, 412, 414, use a peripheral device such as keyboard or mouse, or speak the options text if the display screen 102a, 102b has voice recognition capability).

FIGS. 5-10 illustrate embodiments of various screens that can display based on the patient's content choice on the menu screen 500 (or on another screen since mode and content choices may be made available on various screens). The screens illustrated herein are provided as non-limiting examples; screens can have any configuration and one or more additional screens may be provided to the patients 112a, 112b before or concurrent with these content-specific screens, e.g., required viewing content as further described below.

The screens 400, 500, 600, 700, 800, 900, 1000 can each include one or more navigational features (in addition to or instead of those described for specific ones of the screens 400, 500, 600, 700, 800, 900, 1000) such as a home button 506 to access the menu screen 400, a back button 508 to return to the previously viewed screen, a help button 510 (which may provide help regarding the currently viewed screen and/or other features of the touch screen 102a, 102b and its user interface), and other similar types of navigational features. The navigational features can be located anywhere on the screens 400, 500, 600, 700, 800, 900, 1000. On-screen instructions 516 particular to the currently viewed screen may or may not be provided by default. Scroll buttons (e.g., page up/down buttons, previous/next buttons) can be provided and used if more options are available for selection than can be contemporaneously displayed on any given screen. Any selected option on any screen can open a screen in a new window or in the same window as the screen from which it was selected. Based on the option selected, a user input mechanism may appear on (or disappear from) the screen to ease use of the selected application (e.g., a keyboard appears for use with a crossword puzzle or a numeric keypad appears for use with a multiple choice-based survey).

Color schemes and/or images on the display screen 102a, 102b can be used to help reduce the chance of operator error. For example, in the illustrated embodiment of the menu screen 500, the graphics 402a, 404a, 406a, 408a, 410a, 412a, 414a have different images, e.g., a television 402a for television content and cards 410a for games content. In the illustrated embodiment of the menu screen 500, the text options 402, 404, 406, 408, 410, 412, 414 have the same color scheme, but each content choice can have a different color scheme. The color scheme can be used as a reference by the patient 112a, 112b during use of the touch screen 102a, 102b for determining/confirming which content he/she has selected, e.g., by having a screen background color match the chosen option's color scheme.

One skilled in the art will appreciate that a variety of patient information can be entered with the methods and devices described herein and that the display on the touch screen 102a, 102b can be adapted depending on the intended use. To facilitate data entry and reduce risk of operator error using the touch screen 102a, 102b, the processor 104 can render only necessary keypad and/or button icons on the touch screen 102a, 102b. Thus, where data entry for an input field selected by the operator (or otherwise activated) requires only numeric values, the processor 104 can renders only a numeric keypad on the display 102a, 102b. Conversely, where an alphanumeric input field is selected by the operator (or otherwise activated), the processor 104 can renders a full (alphanumeric) keypad on the display 102a, 102b. As the operator moves from one data entry type to another, the processor 104 can changes the icons (or data entry widgets), as necessary, even on the same screen. For example, when a text entry widget is activated, a keyboard can be rendered by the processor 104 on the touch screen 102a, 102b. Conversely, when a numeric entry field is activated, a keypad can be rendered.

The screens discussed herein are not limited to any particular layout or configuration. For example, manipulation tools such as touch-activated icons, pulldown menus, tabs, buttons, selection boxes, and scrollbars can be implemented using any type of manipulation tool. Furthermore, two or more screens may be combined and presented on a single screen and one screen may be divided into two or more screens. There may also be additional screens. Furthermore, users may manipulate the screens in any way, e.g., using a mouse, a touch screen, a stylus, keyboard commands, etc. For example, a user may move his or her mouse pointer over an icon and click on the icon to access a particular functionality.

Figure 5:
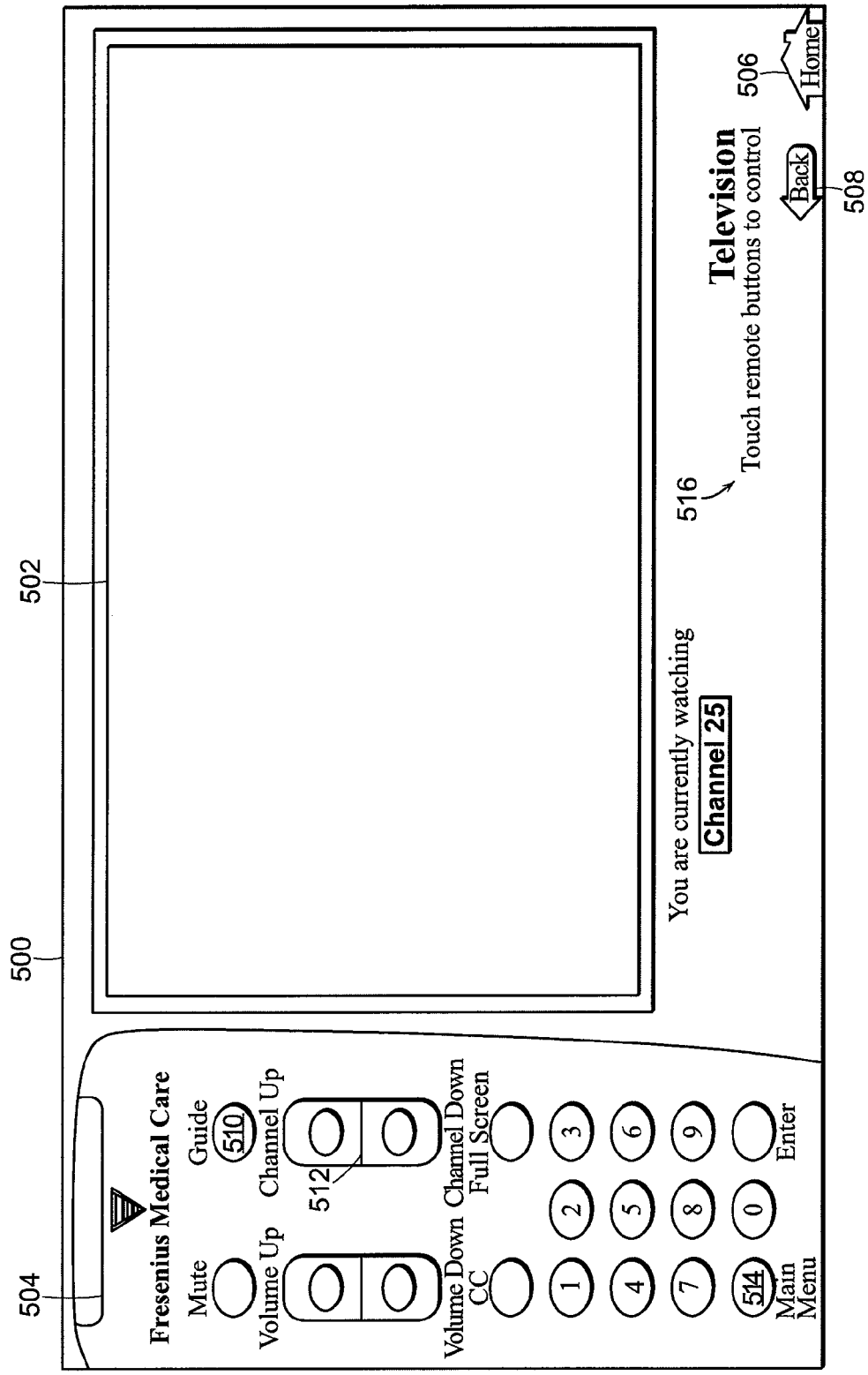
FIG. 5 depicts a television screen display of a digital data display device according to the invention that facilitates selection of data for display.

Referring first to FIG. 5, upon selection of the television text 402 or graphic 402a, the touch screen 102a, 102b can display a television viewing screen 500. The television viewing screen 500 can display a television screen 502 that shows television channels like an ordinary television, pre-stored television programs, and the like. Content for the television screen can be delivered to the touch screen 102a, 102b from the television data 202 (FIG. 2) or from another source, e.g., a cable or satellite connection.

The television viewing screen 500 can be programmed to initially display to the patient 112a, 112b on a specified channel or with a specified video/audio introduction, or the patient 112a, 112b may be able to immediately choose television content on the television viewing screen 500. The patient 112a, 112b can choose content for display on the television screen 502 by, for example, touching buttons on a remote control style menu 504 on the television viewing screen 500. The remote control 504 can include, among other options, channel up/down buttons 512 and a main menu button 514 to access a television home page (e.g., a guide of available channels). Content 202 for display on the television screen 502 is typically the same for different patients 112a, 112b, but the television data 202 may be based at least on identification of the patients 112a, 112b as described further below, e.g., restricting users under a certain age to particular television channels.

Figure 6:
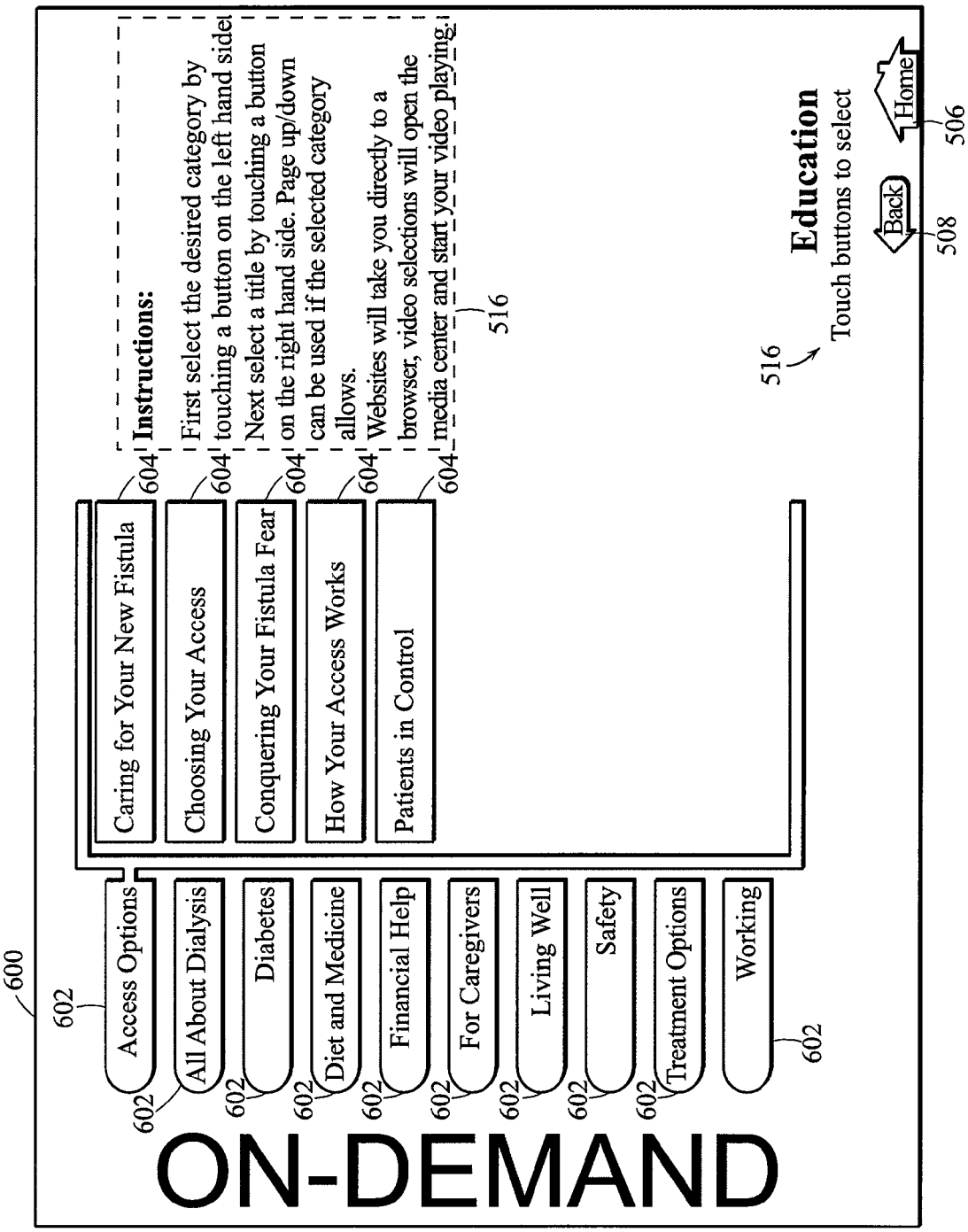
FIG. 6 depicts an education screen display of a digital data display device according to the invention that facilitates selection of data for display.

If the education option 404, 404a is chosen (FIG. 4), then the touch screen 102a, 102b can display an education screen 600 as shown in FIG. 6. The education screen 600 can include the education data 212 (FIG. 2) displayed as one or more education content options 602, which can be presented textually or graphically as described above regarding the main menu screen 400. In this example, the education options 602 are shown as a vertical list of text buttons. The education options 602 can be catered to a particular user of the touch screens 102a, 102b (as identified by login via the entry screen 300 of FIG. 3) as described further below.

Non-limiting examples of the education options 602 include treatment information (e.g., dialysis access options, educational information regarding treatment at the dialysis machines 110a, 110b, treatment options, etc.), diagnosed patient conditions (e.g., diabetes, high blood pressure, etc.), self medical care issues (e.g., diet and medicine, living well, safety, etc.), financial help, caregivers, working/employment issues, and similar types of educational information. Upon selection of one of the education options 602, another menu of category specific education options 604 can appear, e.g., on a new screen, on the education screen 600 in tree format to the right of the selected option (as shown), or otherwise. The category specific education options 604 can also be catered to a particular user as explained below. The education option 602 to which the displayed category specific options 604 apply may be highlighted, such as by changing its color, changing its appearance to look as if it has been depressed, or otherwise highlighting the education option 602 (as shown, the selected access options button 602 is ringed in green).

Figure 7:
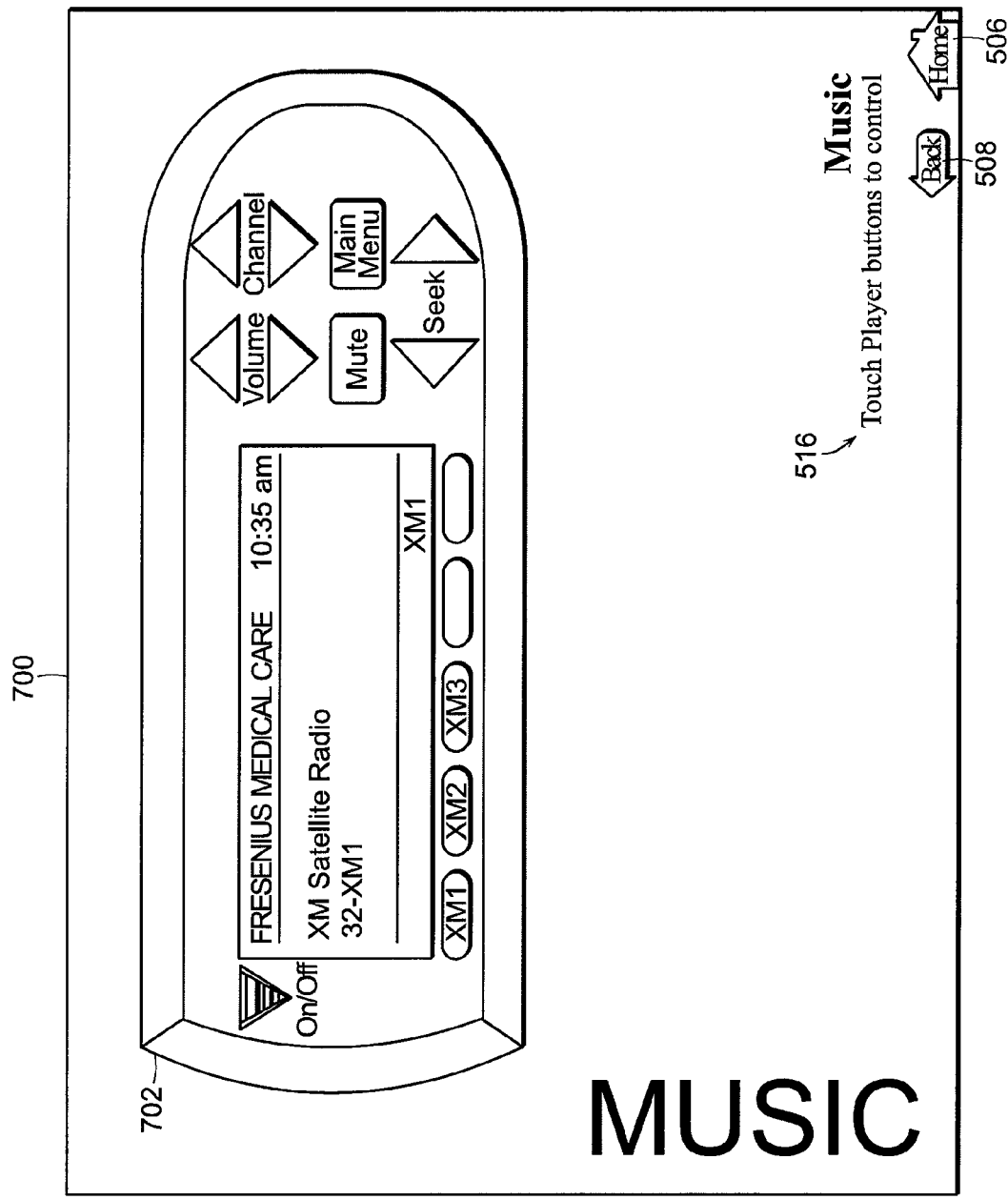
FIG. 7 depicts a music screen display of a digital data display device according to the invention that facilitates viewing of data.

Although not always specifically mentioned with regard to particular screens, category specific options can be available on any screen, e.g., choices of music genres, radio stations, pre-programmed playlists, etc. upon selection of the music option 412, 412a prior to accessing the music screen 700 of FIG. 7.

The music screen 700 can include an audio player 702 which can play music and/or other types of audio. The audio player 702 can play music data 210 from the content database 108 and/or other audio content, such as radio stations (accessed like a traditional radio or over a network such as the Internet) and recorded audio (e.g., compact discs, digital music, etc.). The patients 112a, 112b may be able to provide music content for play through the audio player 702, e.g., by interfacing a portable music player to the display device 102a, 102b.

Figure 8:
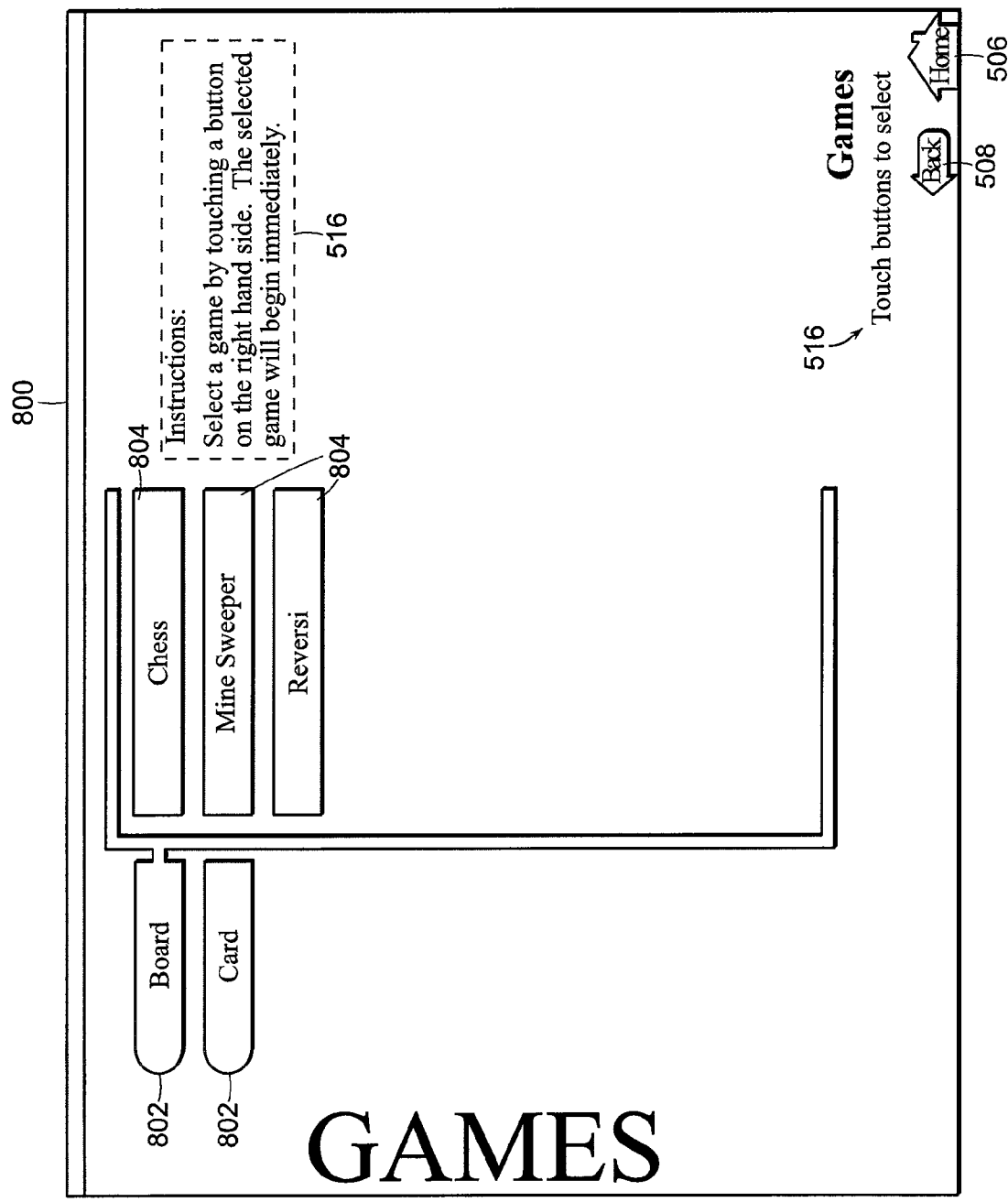
FIG. 8 depicts a games screen display of a digital data display device according to the invention that facilitates viewing of data.

Referring to FIG. 8, if the games option 410, 410a is chosen (FIG. 4), then the touch screen 102a, 102b can display a games screen 800. The games screen 800 in this example initially presents game category options 802 (e.g., board, cards, sports, word, educational, etc.), which when selected trigger display of game options 804 within the selected category. The games screen 800 may not list game category options but instead present a list of all games, organized alphabetically, by approximate game completion time, by favorites as indicated by previous choices by the patient 112a, 112b, or other organizational scheme. The game options 804 can include traditional games (e.g., solitaire, chess, Mine Sweeper, Reversi, hearts, poker, checkers, crossword puzzles, baseball, pinball, etc.) and/or educational games designed to educate in game format (e.g., word searches or Hangman using medical terms, trivia, constructing nutritionally appropriate meals within a certain time limit or given various food options, etc.).

Patients 112a, 112b under a certain age may only receive educational game options or may receive educational game options when they select the education option 404, 404a. When the patient 112a, 112b selects one of the game options 804, the game can start immediately, or rules may first be made available. Additionally, the patients 112a, 112b may be able to play games against each other, e.g., coordinated and/or hosted by the processor 104 and using the communication links 120.

Figure 9B:
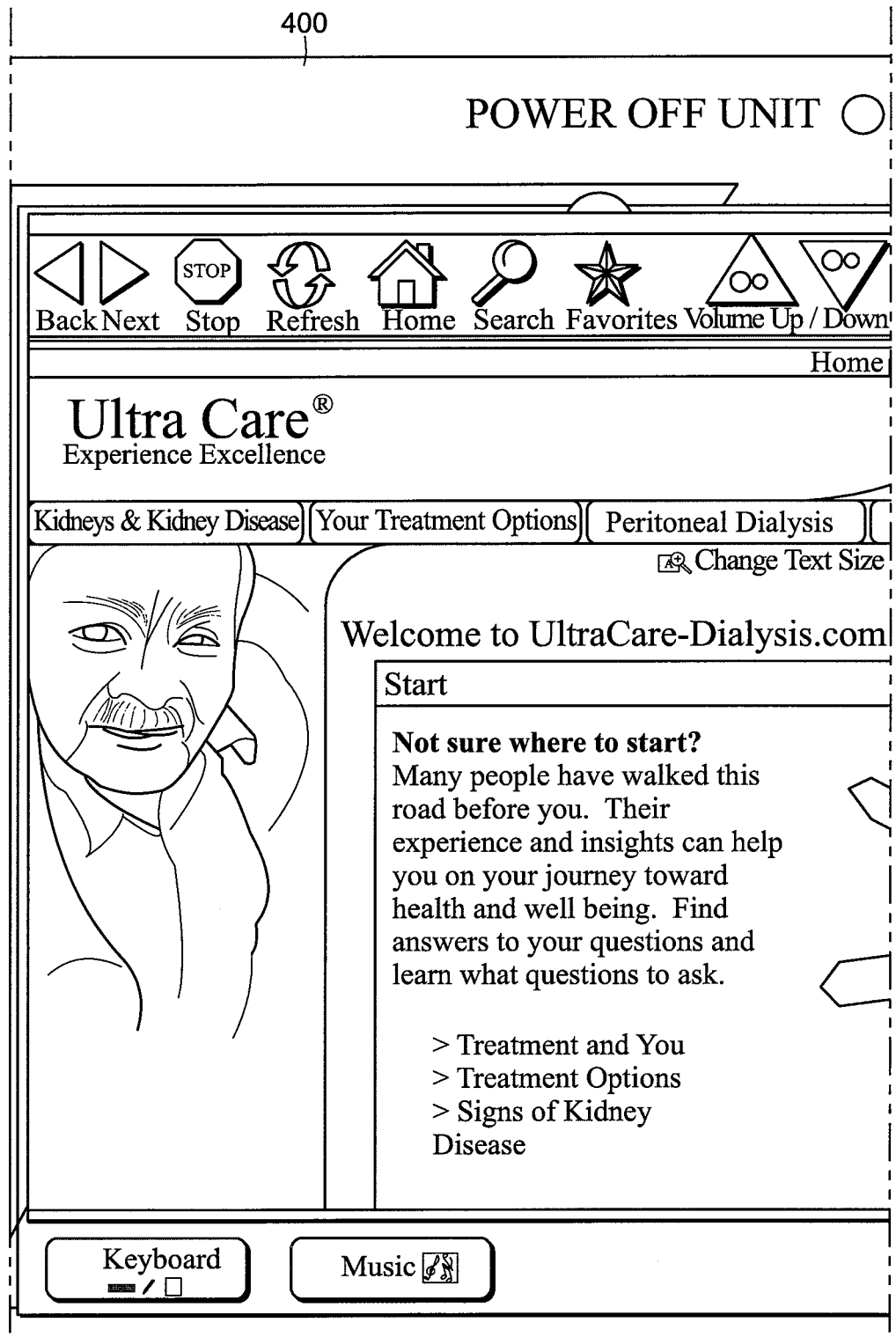
FIG. 9 depicts an Internet screen display of a digital data display device according to the invention that facilitates viewing of data.
Figure 9C:
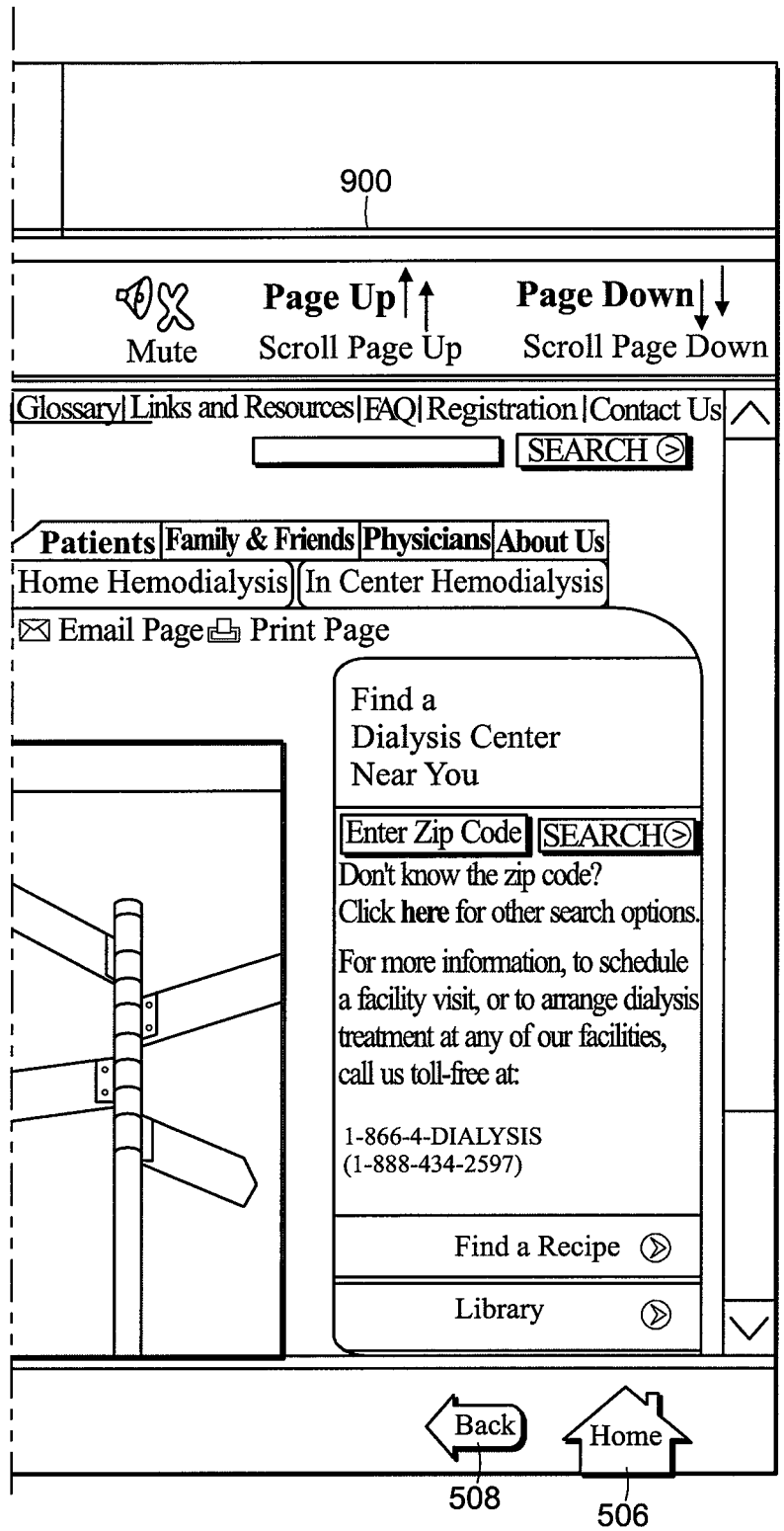

Referring to FIG. 9, if the internet option 406, 406a is chosen (FIG. 4), then the touch screen 102a, 102b can display an Internet screen 900. The Internet screen 900 is shown as a separate, pop-up window from the menu screen 400 from which it was selected. The Internet screen 900 can function like any browser, as is well known in the art. The Internet screen 900 can provide access to any one or more networks, such as the Internet, an intranet, an extranet, and any other similar type of content-providing network. The network(s) available through the Internet screen 900 can be direct-connected and/or networked to the processor 104 and/or interface 102a, 102b.

Figure 10:
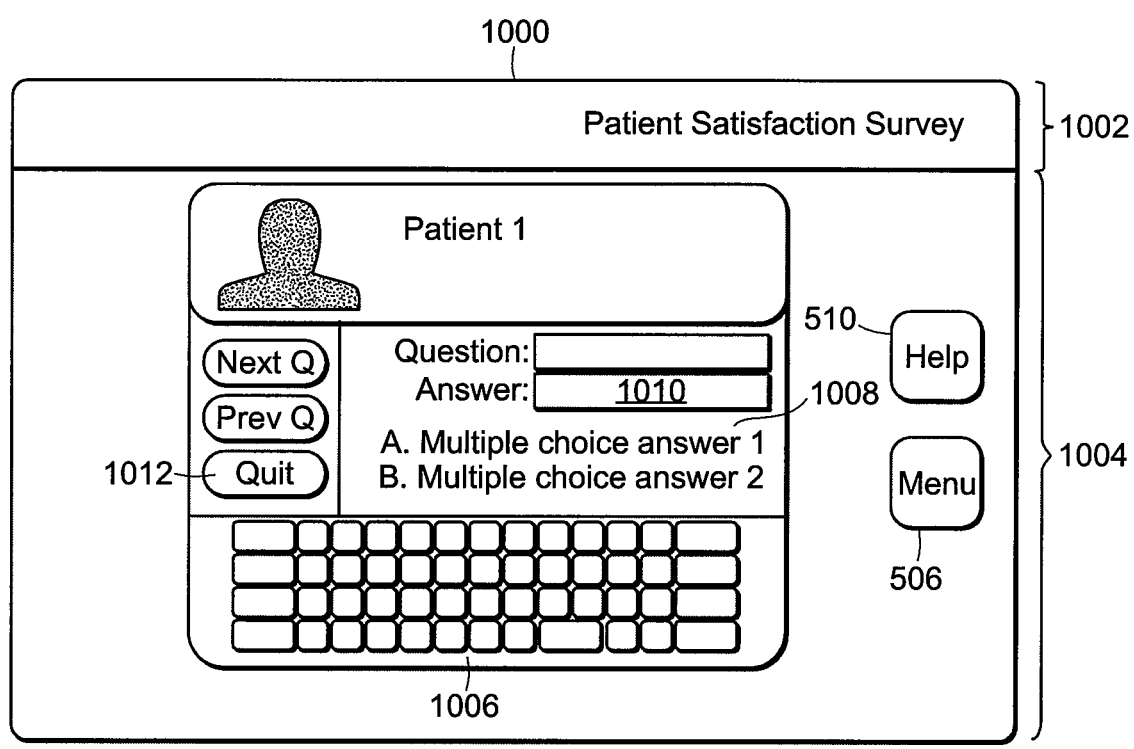
FIG. 10 depicts a survey screen display of a digital data display device according to the invention that facilitates viewing of data.

Referring to FIG. 10, if the surveys option 408, 408a is chosen (FIG. 4), then the touch screen 102a, 102b can display a surveys screen 1000. The surveys screen 1000 illustrates a survey in progress. Before displaying the surveys screen 1000, the touch screen 102a, 102b may first display one or more choices of surveys that the patient 112a, 112b can choose to begin (new surveys) and/or complete (in-progress surveys). Surveys can include any question/answer type interaction, such as a feedback form a questionnaire, or other interrogatory process regarding any aspect of patient care such as how the patient 112a, 112b is feeling, the patient's response to treatment, the patient's understanding of his/her treatment and condition program, the patient's understanding of what he/she should be doing in connection with his/her treatment program, functionality of the station 100a, 100b and other similar types of questioning.

In this embodiment, the surveys screen 1000 includes a title bar 1002 indicating the content being viewed and a content window 1004 showing the actual content. The screens displayed to a particular patient typically have the same general configuration (color scheme, font, button locations, etc.), e.g., the surveys screen 1000 having the same configuration as the music screen 700 (unlike in these illustrated examples where the surveys screen 1000 and the music screen 700 have different configurations). The surveys screen 1000 includes a keyboard 1006 which the patient 112a, 112b can use to enter one of the provided choices 1008 in an answer box 1010. Alternatively, the user may be able to touch one of the provided choices 1008 by way of answer. One or more survey navigation buttons 1012 can be provided which can allow the patient 112a, 112b to, for example, return to the previous question, move to the next question, or quit the survey.

Figure 11:
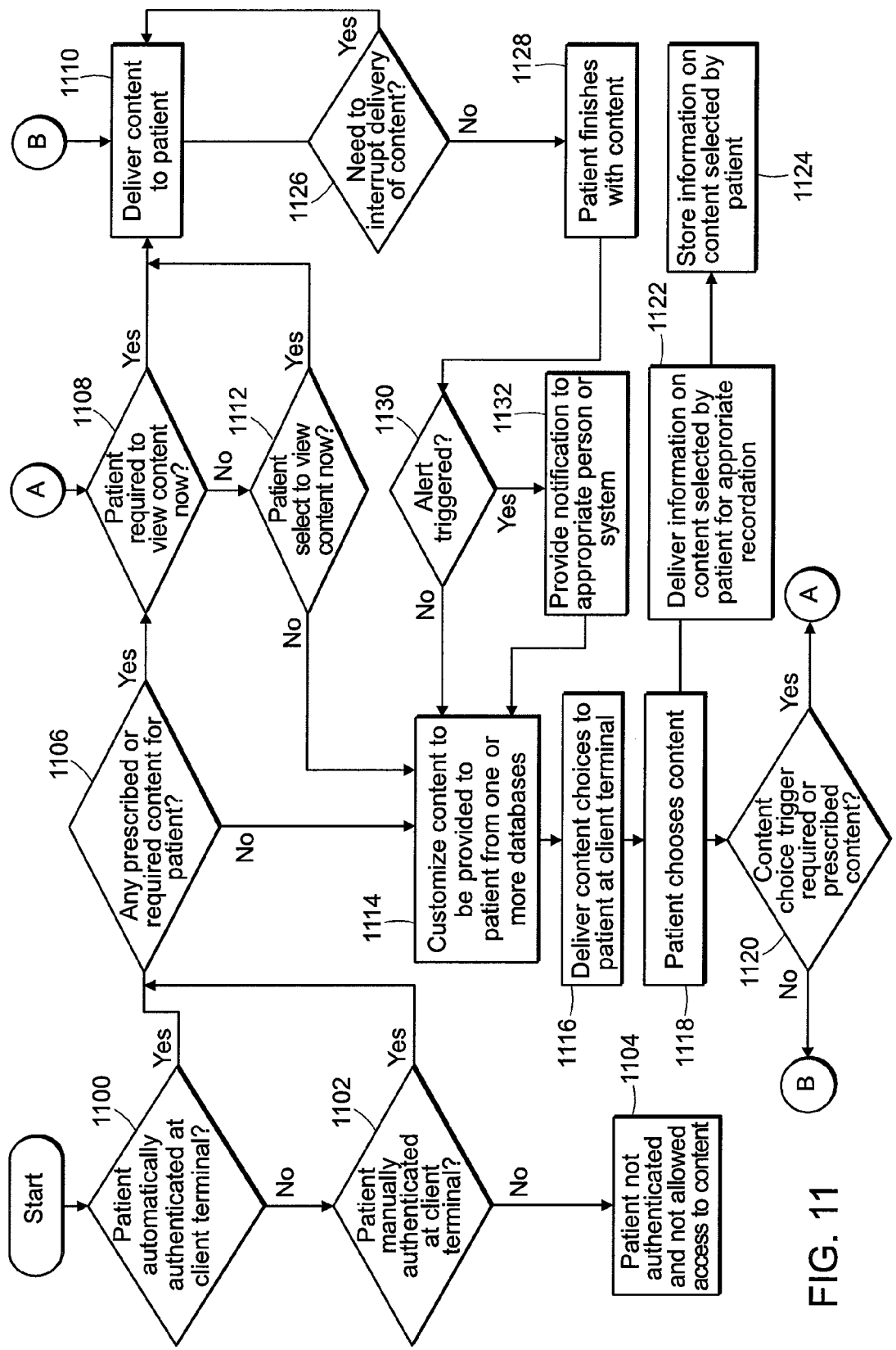
FIG. 11 depicts a workflow for data display in a system according to the invention.

FIG. 11 is a system flow diagram illustrating the use of a system to transfer condition-based information to and/or from a user (and, more particularly, to the display devices 102a, 102b). Although the system flow diagram is described with reference to the elements included in the embodiment of FIG. 1, this or a similar process, including the same, more, or fewer steps, reorganized or not, may be performed using the system of FIG. 1 or using another, similar system. Furthermore, for simplicity of discussion, the system flow diagram is described with reference to the left patient treatment station 100a, although the same can apply to the right patient treatment station 100b (and any other station as described herein).

As shown in the drawing, the processor 104 determines 1100 if the patient 112a has been automatically authenticated at the left patient treatment station 100a, and more particularly at the display device 102a. Authentication of the patient 112a can allow the processor 104 to provide customized information to the display device 102a based on the patient 112a currently using the display device 102a. Authentication can also help assure that only authorized users can access data, some of which may be confidential medical information, available at the display device 102a via the processor 104.

Automatic authentication can occur, for example, if an administrator authenticates the patient 112a by identifying the patient and entering authorization clearance at the touch screen 122. In another example, the patient 112a may be wearing or carrying an automatic authorization mechanism such as a radio frequency identification (RFID) tag that the display device 102a and/or the processor 104 can automatically detect when the patient 112a is within sufficient proximity. In yet another example, the machine 110a may be programmed for the patient 112a, and the processor 104 can identify the patient based on the machine's programming.

If the patient 112a has not been automatically authenticated, then the processor 104 determines 1102 if the patient 112a can be manually authenticated. Manual authentication can occur using the entry screen 300 described above. If a first attempt at authentication fails, the patient 112a may receive one or more additional attempts to log on to the system, although the number of additional attempts may be limited. If the patient 112a cannot be manually authenticated, the processor 104 denies 1104 the patient 112a any further access to content through the display screen 102a. The processor 104 can also optionally trigger an error message or alert to be sent to an administrator, or more specifically to the touch screen 122 or other device, so an administrator can assist the patient 112a with login.

Once authenticated either automatically or manually, the processor determines 1106 if there is any required or prescribed content to be displayed to the patient 112a on the touch screen 102a. Required or prescribed content can include any content that has been recommended or prescribed (typically by a physician or other health care provider) for the patient 112a to view, either at the time it is presented or at a later time, typically during the same treatment session in which it was first presented to the patient 112a. The required or prescribed content can be specific to the patient 112a (e.g., regarding a recently prescribed medication or an aspect of treatment) or it can be general (e.g., how the machine 110a works). The processor 104 may consider the patient's location in determining whether required or prescribed content exists because, for example, patients are typically at clinical centers such as dialysis centers for a limited period of time during which content can be delivered, so content may be required viewing so as to help ensure that the patient 112a receives certain information during the instant clinic visit.

By way of non-limiting example, required or prescribed content can include educational materials regarding treatment prescribed by medical personnel (e.g., a physician, social worker, dietician, etc.), instructions regarding the patient treatment station 100a, question of the day, tip of the day, appointment reminders or recommendations, and other types of similar content.

If the processor 104 determines that there is required or prescribed content for the patient 112a, the processor 104 determines 1108 if the patient 112a must view the required or prescribed content now, i.e., before the patient 112a can choose content for viewing on the touch screen 102a and/or before the touch screen 102a displays content option choices (e.g., the menus screen 400) to the patient 112a. If the patient 112a must view the required or prescribed content at the instant time, then the processor 104 retrieves the required or prescribed content from the appropriate one or ones of the databases 106, 108 and delivers 1110 the required or prescribed content to the touch screen 102a for display to the patient 112a. If the patient 112a need not view the required or prescribed content at the instant time (e.g. because the patient 112a can choose to view the required or prescribed content anytime within a certain amount of time, such as a week), the patient 112a can be presented with the option to view the required or prescribed content.

The processor 104 can determine 1112 whether the patient 112a selects to view the required or prescribed content by, e.g., receiving an input signal from the touch screen 102a. If the patient 112a selects to view the required or prescribed content, then the processor 104 retrieves the required or prescribed content from the appropriate one or ones of the databases 106, 108 and delivers 1110 the required or prescribed content to the touch screen 102a for display to the patient 112a.

Figure 12:
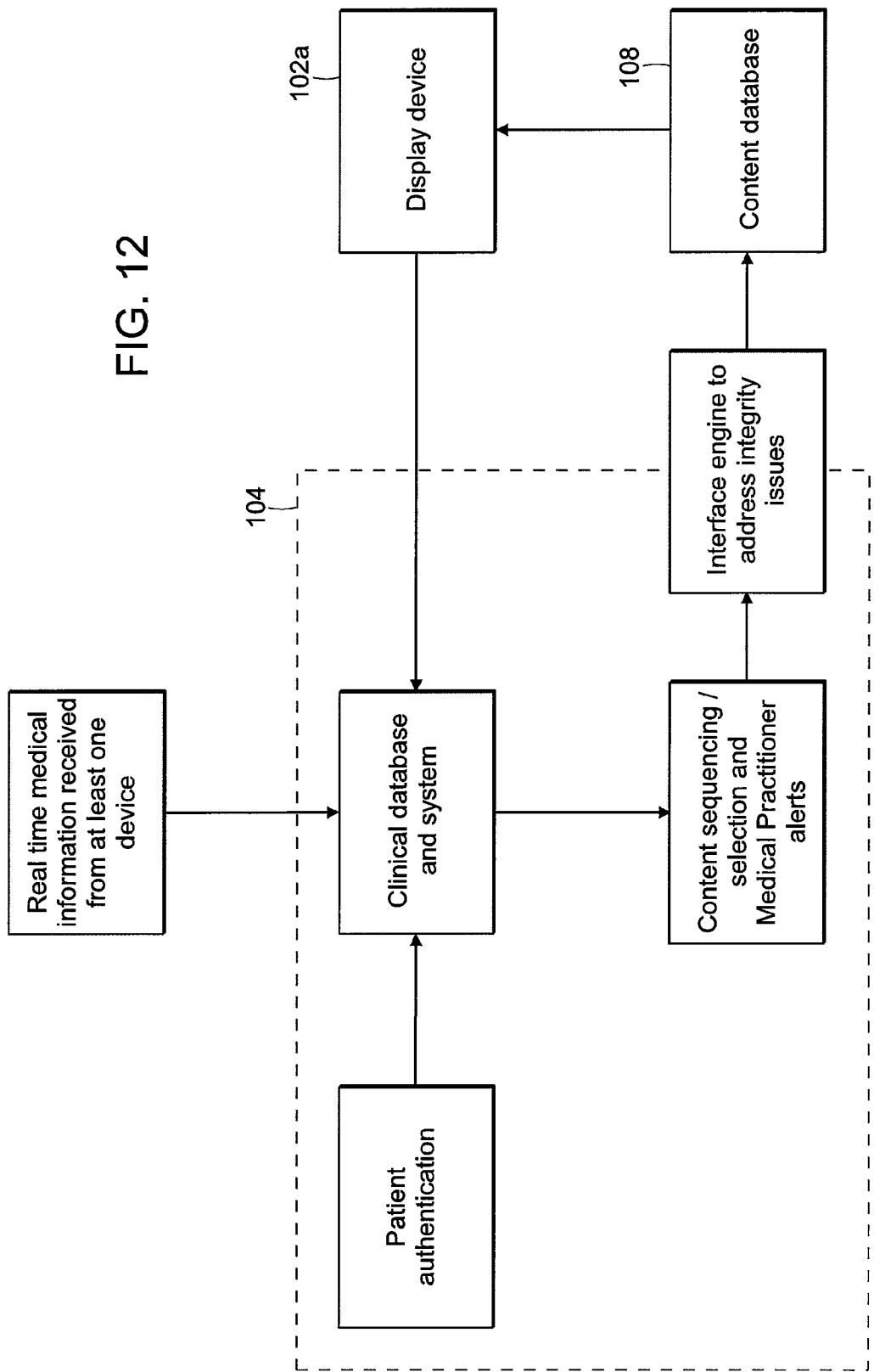
FIG. 12 depicts a schematic diagram of system according to an invention that facilitates selection and transmission of data for display on a digital data display device.

If the patient 112a does not select to view the required or prescribed content, or if there was not any required or prescribed content for the patient 112a, then the processor 104 customizes 1114 content to be retrieved from and provided to the patient 112a from one or both of the databases 106, 108 (typically, the content database 108). One skilled in the art will appreciate that the content for delivery to the screen 102a can be chosen with a variety of schemes that extrapolate, average, and/or rank content based on such factors as current patient data, previous patient data, and/or "normal" patient values. FIG. 12 illustrates one embodiment of the processor 104 and elements which can receive real time data (e.g., from the machine 110a, from the screen 102a, etc.), analyze data to determine content delivery, and deliver content to the touch screen 102a.

Still referring to FIG. 11, at the beginning of patient treatment, i.e., typically immediately following authentication of the patient 112a, the processor 104 may choose content for delivery based on real-time data (e.g., blood pressure, etc.) but also on non-real-time and/or historical data. For example, the processor 104 can consider archived patient medical data (such as that stored in the medical database 106) indicating diagnosed diseases, previous diet instructions, currently prescribed medications, composition of used or spent dialysate, and the like, and deliver specifically related educational information.

For another example, the processor 104 can consider the patient's current medical condition (e.g., as measured by the treatment apparatus) and/or the patient's compliance with one or more requirements, goals, or milestones in determining content choices to present on the display screen 102a. Whether the patient 112a has complied with a requirement, met a goal, or met a milestone can be stored in the database 106 (or other location accessible by the processor 104), and the processor 104 can grant or deny the patient 12a access to particular content from the content database based on the patient's compliance. For example, after viewing a certain type or amount of educational and/or required material, a new entertainment option such as the Internet can be made an available mode choice as a "reward" to the patient 112a. For another example, if the patient 112a has met a treatment-related goal, such as appearing for all scheduled hemodialysis appointments within a certain time period (e.g., one month) or demonstrating a reduced potassium level over time, then the patient 112a may be granted a reward such as free access to otherwise fee-based content such as cable television or coupons to stores (which may be electronically redeemed using the screen 102a or provided in hard copy to the patient 112a). For yet another example, if the patient 112a previously failed to comply with a requirement or failed to meet a goal, then the processor 104 may deny the patient 112a access to particular content, e.g., games, premium cable television channels, etc. Access to denied content may be restored in real time, such as if the patient 112a views an educational video on the screen 102a or discusses a missed goal with a medical practitioner who may manually restore patient content access via the screen 122.

Once the processor 104 has determined content for the patient 112a, the processor 104 can deliver 1116 the content to the patient 112a (or, more specifically, the touch screen 102a). This delivered content here generally includes choices of content (video, audio, games, etc.) that can be delivered from the content database 108 upon selection by the patient 112a, such as a customized menu of options on the main menu screen 400 or customized educational materials available through the education screen 600.

Presented with two or more content options, the patient 12a can choose 1118 via the touch screen 102a content he/she wishes to access. The patient's choice can be communicated to the processor 104, which can determine 1120 whether the patient's content choice triggers delivery of required or pre-scribed content. The processor 104 can also optionally deliver 1122 information identifying the content selected by the patient 112a to an appropriate location for appropriate recordation 1124 (e.g., to one or both of the databases 106, 108 where it may be later accessed by the processor 104 to determine content for delivery to the patient 112a, or even to other patients since the processor 104 may choose content based on popularity among patients having similar medical conditions). If no required or prescribed content is associated with the patient's choice, then the processor 104 can deliver 1110 the selected content to the display screen 102a.

Delivery of required or prescribed content may be triggered for a variety of reasons, such as requiring the patient 112a to view instructions for a game or audio player before being allowed to access it or requiring a patient to watch part one of an educational video before allowing them to watch a subsequent part of the video. If delivery of required or pre-scribed content is triggered by the patient's selection, the required or prescribed content can be delivered to the touch screen 102a as described above (including not necessarily providing to the patient 112a at the instant time).

Customization of content for delivery 1110 can be an ongoing process for the processor 104. For example, the processor 104 can receive real time medical information from the machine 110a (and/or other device, e.g., a standalone blood pressure monitor or supplemental oxygen device) regarding a current medical condition of the patient 112a. Non-limiting examples of real time medical information include blood pressure, heart rate, blood potassium level, content analysis of fluids transferring in and out of the patient 112a during dialysis treatment, and other types of similar information that may be monitored and/or catalogued regarding the patient 112a. Real time medical information can be communicated from machine 110a to the processor 104 for storage in the medical database 106 where it can be accessed at a later time, possibly for analysis regarding medical trend information that may be used by the processor 104 to determine what content to deliver to the patient 112a during the instant or subsequent treatment.

Considering real time medical information and/or other factors such as a duration of the instant treatment session and a history of Internet websites visited, the processor 104 can determine 1126 if there is any need to interrupt delivery of content to the patient 112a. Interruption may be necessary for a variety of reasons. For example, real time medical information regarding the patient 112a received at the processor 104 may trigger delivery of content, e.g., a blood pressure measurement above a certain predetermined level (generally or specific to the patient 112a) may trigger a delivery of a message to the patient 112a that a high blood pressure level has been detected and that they should attempt corrective action such as reclining. In another example, the machine 110a may begin a new stage of treatment or be nearing end of treatment, and the processor 104 can send an alert to the patient 112a informing him/her of the treatment's progress. In yet another example, a high potassium level measurement may trigger delivery of dietary information on how to reduce potassium levels in the blood, including lists of foods to avoid eating and cooking recipes.

If interruption of content delivery to the touch screen 102a is necessary, then the processor 104 can deliver 1110 the newly determined content to the patient 112a. The content viewed by the patient 112a at the time of interruption may be paused for continuation at a later time. If there is no need for interruption, the patient 112a can finish 1128 viewing the content, e.g., finish playing a game, finish watching a video, listen to music until the patient 112a stops it, read educational pamphlet material, browse the Internet until the patient 112a closes the browser, etc.

After the patient 112a finishes 1128 viewing particular content, the processor 104 can customize 1114 a new set of content (e.g., menu options) for delivery to the patient 112a, or the processor 104 can provide previously determined content. However, based on the content the patient 112a finished, an alert may be triggered, so the processor 104 determines 1130 if an alert is triggered and, if so, provides 1132 notification of the alert to an appropriate person or system. Alerts can be triggered for a variety of reasons. For example, the patient 112a may have completed a survey, and an alert may be sent to inform an administrator to forward the survey results to an appropriate survey coordinator. For another example, particularly if the patient 112a is under a certain age, finishing a game with a score above a certain level may trigger an alert to be sent (e.g., via electronic mail, text message, phone, pager, illuminating a light proximate to the display screen 102a and/or the touch screen 122, etc.) to an administrator in the treatment room who can deliver a prize to the patient 112a. For yet another example, if the patient 112a views a particular educational video, an alert may be sent to an administrator in the treatment room to provide the patient 112a with particular materials (e.g., further reading, materials useful in implementing a taught procedure, etc.) when the patient 112a finishes treatment at the machine 110a.

Described above are devices and systems meeting the aforementioned objects, among others. Those skilled in the art will appreciate that the embodiments discussed and shown herein are merely examples of the invention and that other embodiments fall within the scope thereof. Thus, by way of non-limiting example, it will be appreciated that a patient treatment station of the type described above can be used with a variety of medical treatment and diagnostic apparatus, in addition to dialysis machines. By way of further example, it will be appreciated that, in some embodiments (e.g., where sanitary conditions are of less concern and/or are compensated for in other ways), the touch screen can be replaced by a conventional display (e.g., cathode ray tube (CRT), liquid crystal display (LCD), or otherwise) and a keyboard. A further appreciation of the invention may be attained by reference to the following appendices.

Appendix I

| DirectTouch ™ segment from the Clinic of The Future Presentation | | | | |
|---|---|---|---|---|
| VOICEOVER Script | What is Happening | Nurse | PCT | Patient |
| Welcome to the Clinic of The Future! Let's visit this PAPERLESS Clinic, where ALL patient information is entered and available online. We'll see how our new eCube Clinical system supports patient care management and clinical decision making. We'll see how the CHAIRSIDE system frees up the clinic staff to spend more time with the patient. Finally, we'll see how our patients use the new DirectTouch Patient Entertainment System, as we deliver on the Ultra-Care promises of Individual Patient care and excellent customer service. (non Direct Touch segments of script deleted for clarity) | Welcome Voice Starts while lights go down | Standing at workstation | Standing at chairside | Lying in Chair |
| We've been taking care of Gretchen, but let's see what she's been so busy doing! With the new DirectTouch Patient Entertainment System, Gretchen has access to digital radio, satellite TV, movies, games, educational material, and the internet. Gretchen, do you mind showing us the DirectTouch system? Hi! Let me show you how I use this! It's a touchscreen so I just pick exactly what I want from the menu. The best thing about this system is that I get to watch what I feel like - sometimes it's a movie, and sometimes it's a video to help me understand how to eat right . . . My dietitian says I'm doing a much better job these days managing my Po-tah-see-um . . . I think it's really helped to review the rules right here whenever I want to. And here's something I didn't expect - satellite radio! | | Moves away from chairside | Moves away | Touches monitor screen Acts like she is singing |
| OH! I love this song! [she listens for a few seconds - Abba - take a chance on me . . . ] dah-dah-dah I don't suppose we have time to listen to the whole thing . . . it reminds me of a handsome Swedish gentleman I met once. | | Moves away from chairside | Moves away | Touches monitor screen Acts like she is singing |
| Let's see - where next? Surveys? That's where I can let the staff know how things are going, and so on. But let me show you the games - this really helps when the treatment seems long . . . There's card games and also board games - I'm getting pretty good! And I can even access the internet! It's neat, and I guess I'm going to use this a lot in the future. I think I've covered it all - so let me just say thank you to all of you at Fresenius Medical Care - this makes my treatment time just fly by. Now I think I'll get back to my movie if you don't mind! Thanks for stopping by! (non DirectTouch segments of script deleted for clarity) | | Nurse walks over near Mary | | Goes back to pressing touchscreen. Then glances at crowd and gives thumbs up at monitor. |
| We hope you've enjoyed your visit to the Clinic of The Future! We've seen how CHAIRSIDE. DirectTouch, and eCube will help you provide the best UltraCare ever to YOUR patients. There's many more clinical managers waiting to come in and see all of this, so please help us by existing quickly through the SIDE doors on EITHER side, and down the hallways back into the exhibit hall. DO not exit by the doors you came in. PLEASE exit through the side doors. | | Start move audience toward exit doors and start positioning next group | Start move audience toward exit doors and start positioning next group | |

Appendix II
  The clinical database includes:
    Etiology—information on ethnicity, demographics, lab results, treatment history, treatment plans, etc.
    Real-time data from sensors (vital signs, blood pressure, etc.), Hemodialysis equipment, Chairside. Survey input, web camera (retinal tracking to record patient activity)
  Features of Selection Process:
    Can be mandatory videos, such as one on potassium levels.
    Survey may trigger other required or recommended content
    Can periodically (for example, every hour) require additional content to be received/viewed.
    Appointments with dieticians or other healthcare providers can be recommended or required.
    Educational games such as constructing a nutritionally appropriate meal should/could be included; can play against others.
    Can be based on information from tracking Internet searches, TV viewing, or other content or activities of the patient. For example, by tracking web surfing and/or chatroom activity it may be determined that the patient is seeking information on treating headaches and information on headaches could be provided or required.
  Benefits:
    Patients more likely to take treatments as prescribed and complete treatments.
    Provides alternate focus from pain; makes treatment a less painful experience
    Improves patient compliance with treatments
    Improves therapeutic outcomes
    Improves patient care results may increase physician compensation/reimbursement
    Improves patient interactivity/communication with healthcare provider
    Enhance patient self-care
    Enhance provider responsiveness
      In view thereof, what we claim is:

What we claims is:

1. A method of delivering patient-specific content, comprising:
   detecting a current medical condition of a patient receiving medical treatment from a medical treatment apparatus coupled to the patient;
   selecting any of required and prescribed content for delivery to a data display device associated with the medical treatment apparatus based on the current medical condition of the patient
   enabling the patient to choose entertainment content;
   delivering the selected required or prescribed content to the patient via the data display device;
   delivering the patient-chosen entertainment content to the patient via the data display device;
   wherein the patient-chosen entertainment content is delivered to the patient via the data display device only after delivery to the patient via the data display device of the required or prescribed content; and
   wherein delivery of either the selected required or prescribed content or the patient-chosen entertainment content is interrupted if a change in the current medical condition of the patient is detected by the medical treatment apparatus, and a message or further prescribed content is delivered to the patient based on that change of condition.

2. The method of claim 1, wherein detecting the current medical condition includes receiving medical monitoring data from the medical treatment apparatus in current communication with the patient.

3. The method of claim 2, wherein receiving the medical monitoring data includes receiving data related to hemodialysis treatment.

4. The method of claim 1, further comprising using a pre-programmed algorithm to select the informational data for delivery.

5. The method of claim 1, wherein the current medical condition includes at least one of blood pressure, heart rate, and blood potassium level.

6. The method of claim 1, wherein the current medical condition includes data related to dialysis treatment being provided to the patient concurrent with the required or prescribed content being delivered to the patient.

7. The method of claim 1, further comprising transmitting the required or prescribed content over the network from a data collection unit to a digital data display device accessible by the patient.

8. The method of claim 7, further comprising authorizing the patient to use the digital data display device before allowing the patient to access the required or prescribed content at the digital data display device.

9. The method of claim 1, wherein the required or prescribed content includes at least one of educational audio information, educational video information, educational material, a survey, and an educational game.

10. The method of claim 1, further comprising enabling a medical care professional to select the required or prescribed content for delivery to a patient based on a specific medical condition and delivering the selected the required or prescribed content to the patient upon detection of the specific medical condition.

11. The method of claim 1, further comprising enabling the patient to select at least one of two or more entertainment content choices based on a current medical condition of the patient and delivering the chosen entertainment content to the patient over the network.

12. A method of delivering patient-specific content, comprising:
   providing a digital data display device associated with a medical treatment apparatus and configured to display data to a patient receiving medical treatment from the medical treatment apparatus;
   authenticating the patient as a valid user of the digital data display device;
   transmitting first data to the digital data display device from at least one database, wherein the first data is any of required and prescribed content chosen for transmission based on at least real time data related to the medical treatment of the authenticated patient;
   allowing the authenticated patient to choose additional entertainment content for transmission from the at least one database to the digital data display device; and
   transmitting said additional entertainment content only after the first data has been presented to the authenticated patient via the digital data display device;
   interrupting the transmission or presentation of either the first data or additional entertainment contact when the real time data related to the medical treatment of the authenticated patient is outside a pre-determined range.

13. The method of claim 12, further comprising allowing the authenticated patient to select entertainment content to view on the digital data display device using a touch screen at the digital data display device.

14. The method of claim 12, further comprising presenting entertainment content chosen by the authenticated patient on the digital data display device.

15. The method of claim 12, wherein the first data is also chosen based on an identity of the authenticated patient.

16. The method of claim 12, further comprising presenting prescribed content to the authenticated patient on the digital data display device prior to presenting data entertainment content selected by the patient.

17. The method of claim 12, wherein said required or prescribed content includes at least one of educational video information, educational audio information, educational games, educational material, and a survey.

18. The method of claim 12, wherein the first data includes at least one of medical record information and medical treatment information.

19. A patient-specific content delivery system, comprising:
a digital data display device associated with a dialysis treatment device that is configured to monitor real time medical information of the patient and configured to display content related to a patient receiving dialysis treatment; and
a data collection unit configured to be in electronic communication with the digital data display device over a network, to store medical data, and to provide the digital data display device with stored content that includes i) any of required and prescribed educational content, and ii) entertainment content,
wherein the digital data display device is configured to enable the patient to choose, after the patient is authenticated at the digital data display device and while the patient is receiving dialysis treatment from the dialysis treatment device, content from the data collection unit to be displayed by the digital data display device, and
wherein the digital data display device displays to the patient chosen entertainment content from the data collection unit only after display to the patient of required educational content from the data collection unit;
wherein the digital display device is configured to interrupt the display of the chosen entertainment or the required educational content when the real time medical information monitored by the dialysis treatment device is outside of a predetermined range.

20. The system of claim 19, wherein the digital data display device includes a touch screen configured to display one or more types of stored medical data that can be selected by the patient through the touch screen for delivery from the data collection unit to the digital data display device.

21. The system of claim 19, wherein the stored medical data includes data related to at least one of a patient's medical test result, medical care plan, medical history, vital signs, dialysis treatment, and organ function.

22. The system of claim 19, further comprising a second data collection unit configured to be in communication with the digital data display device, to store medical treatment data, and to provide the digital data display device with stored medical treatment data.

23. The system of claim 22, wherein the stored medical treatment data includes data related to at least one of educational video information, educational audio information, educational games, educational material, and a survey.

24. A patient-specific content delivery system, comprising:
a data collection unit configured to store content that includes i) any of required and prescribed educational content related to a medical condition of a patient, and ii) entertainment content; and
a touch screen accessible to the patient receiving medical treatment at a dialysis treatment machine and configured to display the required and prescribed educational content received from the data collection unit, the displayed required and prescribed educational content being displayed concurrent with medical treatment of the patient and being selected for display considering an identification of the patient,
wherein the touch screen enables the patient to choose additional content to be displayed by the touch screen from the entertainment content stored on the collection unit, and wherein the touch screen is configured to display the additional content chosen by the patient only after the required and prescribed educational content has been displayed to the patient and the display of content to the patient is interrupted based on real time medical information regarding the patient.

25. The system of claim 24, further comprising a second data collection unit configured to store medical treatment data, wherein the touch screen is also configured to display data received from the second data collection unit concurrent with the medical treatment of the patient.

26. The system of claim 24, wherein the displayed required and prescribed educational content is also selected for display considering data gathered in real time and in relation to the medical treatment of the patient.

27. The system of claim 24, wherein the touch screen enables the patient to select content from the data collection unit for display on the touch screen and displaying in real time the selected content to the patient.

28. The system of claim 27, wherein the data collection unit is configured to transmit other content for display on the touch screen based on content selected by the patient.

* * * * *